US008236497B2

(12) United States Patent
Doria et al.

(10) Patent No.: US 8,236,497 B2
(45) Date of Patent: Aug. 7, 2012

(54) METHODS OF DIAGNOSING CARDIOVASCULAR DISEASE

(75) Inventors: Alessandro Doria, Cambridge, MA (US); Vincenzo Trischitta, Rome (IT)

(73) Assignees: Joslin Diabetes Center, Inc., Cambridge, MA (US); Istituto di Ricovero e Cura a Carattere Scientifico Ospedale Casa Sollievo Della (IT)

( * ) Notice: Subject to any disclaimer, the term of this patent is extended or adjusted under 35 U.S.C. 154(b) by 580 days.

(21) Appl. No.: 12/066,473

(22) PCT Filed: Sep. 20, 2006

(86) PCT No.: PCT/US2006/036700
§ 371 (c)(1),
(2), (4) Date: Nov. 17, 2008

(87) PCT Pub. No.: WO2007/038155
PCT Pub. Date: Apr. 5, 2007

(65) Prior Publication Data
US 2009/0220954 A1 Sep. 3, 2009

Related U.S. Application Data

(60) Provisional application No. 60/719,435, filed on Sep. 21, 2005.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ...... 435/6.1; 435/91.1; 435/91.2; 536/23.1; 536/24.3

(58) Field of Classification Search .................. None
See application file for complete search history.

(56) References Cited

U.S. PATENT DOCUMENTS 7,435,808 B2  10/2008  Wu et al.
7,598,348 B2  10/2009  Chen et al.

OTHER PUBLICATIONS

Saiki et al; PNAS, vol. 86, pp. 6230-6234, 1989.*
Risch et al; Nature, vol. 405, 2000; pp. 847-856.*
rs10920531 (NCBI, NLM Feb. 2004).*
Motoshima et al; Biochemical and Biophysical Research Communications; vol. 315, 2004; pp. 264-271.*
Database NCBI on STN, rs7539542, dbSNP, "Reliable Identification of large candidate SNPs from public EST data," National Library of Medicine (2003).
Risch et al., "Searching for Genetic Determinants in the New Millenium," *Nature*, 405:847-856 (2000).
Motoshima et al., "Adiponectin Suppresses Proliferation and Superoxide Generation and Enhances eNOS Activity in Endothelial Cells Treated with Oxidixed LDL," *Biochemical and Biophysical Research Communications*, 315:264-271 (2004).
Arita et al., "Adipocyte-derived plasma protein adiponectin acts as a platelet-derived growth factor-BB-binding protein and regulates growth factor-induced common postreceptor signal in vascular smooth muscle cell," *Circulation*, 105:2893-2898 (2002).
GeneBank, database entry #BC010743.1, *Homosapiens* adiponectin receptor 1, mRNA.
Okamoto et al., "Adiponectin reduces atherosclerosis in apolipoprotein E-deficient mice," *Circulation*, 106:2767-2770 (2002).
Ouchi et al., "Novel modulator for endothelial adhesion molecules: adipocyte-derived plasma protein adiponectin," *Circulation*, 100(25):2473-2476 (1999).
Ouchi et al., "Adipocyte-derived plasma protein, adiponectin, suppresses lipid accumulation and class A scavenger receptor expression in human monocyte-derived macrophages," *Circulation*,103(8):1057-1063 (2001).
Pischon et al., "Plasma adiponectin levels and risk of myocardial infarction in men," *JAMA*, 291:1730-1737 (2004).
Saiki et al., "Genetic analysis of amplified DNA with immobilized sequence-specific oligonucleotide probes," *Proc. Natl. Acad. Sci. USA*, 86:6230-6234 (1989).
Schulze et al., "Adiponectin and future coronary heart disease events among men with type 2 diabetes," *Diabetes*, 54:534-539 (2005).
Wang et al., "Adiponectin receptor 1 gene (ADIPOR1) as a candidate for type 2 diabetes and insulin resistance," *Diabetes*, 53(8):2132-2136 (2004).
Yamauchi et al., "Globular adiponectin protected ob/ob mice from diabetes and ApoE-deficient mice from atherosclerosis," *J. Biol. Chem.*, 278:2461-2468 (2003).
Damcott et al., "Genetic variation in adiponectin receptor 1 and adiponectin receptor 2 is associated with type 2 diabetes in the Old Order Amish," *Diabetes*, 54(7):2245-2250 (2005).
Richardson et al., "Association between variants in the genes for adiponectin and its receptors with insulin resistance syndrome (IRS)-related phenotypes in Mexican Americans," *Diabetologia*, 49(10):2317-2328 (2006).
Siitonen et al., "Association of sequence variations in the gene encoding adiponectin receptor 1 (ADIPOR1) with body size and insulin levels. The Finnish Diabetes Prevention Study," *Diabetologia*, 49(8):1795-1805 (2006).
Vaxillaire et al., "Genetic analysis of ADIPOR1 and ADIPOR2 candidate polymorphisms for type 2 diabetes in the Caucasian population," *Diabetes*, 55(3):856-861 (2006).
Furuhashi et al., "Possible Impairment of Transcardiac Utilization of Adiponectin in Patients With Type 2 Diabetes," Diabetes Care, Sep. 2004, pp. 2217-2221, vol. 27, No. 9.
Soccio et al., "Common Haplotypes at the Adiponectin Receptor 1 (ADIPOR1) Locus Are Associated With Increased Risk of Coronary Artery Disease in Type 2 Diabetes,", Diabetes, Oct. 2006, pp. 2763-2770, vol. 55.

* cited by examiner

*Primary Examiner* — Jehanne Sitton
(74) *Attorney, Agent, or Firm* — Pierce Atwood LLP; Joseph M. Maraia; Isabelle M. Clauss

(57) ABSTRACT

Methods are disclosed for diagnosing increased risk of cardiovascular disease in a subject.

11 Claims, 5 Drawing Sheets

| Haplotype | rs7539542 | rs10920531 | rs4950894 | Frequency CAD- | Frequency CAD+ | HaploScore | Hapotype p value | Global p value |
|---|---|---|---|---|---|---|---|---|
| 1 | C | C | G | 0.345 | 0.268 | -3.532 | 0.00035 | |
| 2 | C | C | A | 0.289 | 0.286 | -0.612 | 0.54 | |
| 3 | C | A | A | 0.072 | 0.089 | 1.616 | 0.11 | |
| 4 | G | A | A | 0.274 | 0.320 | 2.293 | 0.021 | 0.0002 |

METHODS OF DIAGNOSING CARDIOVASCULAR DISEASE

CLAIM OF PRIORITY

This application is the U.S. national stage under 35 USC §371 of International Application Number PCT/US2006/036700, filed on Sep. 20, 2006, which claims the benefit under 35 USC §119(e) to U.S. Provisional Patent Application Ser. No. 60/719,435, filed on Sep. 21, 2005, the entire contents of which are hereby incorporated by reference.

GOVERNMENT SUPPORT

The work described herein was carried out, at least in part, using funds from the U.S. government under grants HL73168, HL71981, DK56341, DK60837, and DK36836 awarded by the U.S. National Institutes of Health, and by Italian Ministry of Health grants RC0303ED19 and RC0201ED02. The U.S. Federal government has certain rights in the invention.

BACKGROUND

The adiponectin receptors, ADIPOR1 and ADIPOR2, serve as receptors for both globular and full-length adiponectin and mediate increased AMP-activated protein kinase (AMPK) and peroxisome proliferative activated receptor (PPAR), alpha (PPARα) ligand activities, as well as fatty acid oxidation and glucose uptake by adiponectin (Yamauchi et al., Nature 423:762-769 (2003); Erratum: Nature 431:1123 (2004)). Adiponectin, which is an adipokine facilitating insulin action, has direct protective effects on the arterial wall through inhibition of monocyte adhesion, smooth muscle cell (SMC) proliferation, and foam cell formation. ADIPOR1 is one of the receptors through which adiponectin exerts its anti-atherogenic effects.

SUMMARY OF THE INVENTION

The invention is based, in part, on the inventors' discovery that certain polymorphisms and/or haplotypes within the adiponectin receptor 1 (ADIPOR1) gene correlate with increased risk of cardiovascular disease, e.g., in subjects who have, or are at risk for, type 2 diabetes. Linkage disequilibrium analysis of 28 single nucleotide polymorphisms (SNPs) spanning the entire ADIPOR1 locus revealed two haplotype blocks that could be tagged by six SNPs (see Table 3). These six markers were typed in two populations of coronary artery disease (CAD)-positive and CAD-negative subjects with type 2 diabetes, one from Boston (n=411), the other from Italy (n=533). In the Boston population, the three tags of the more 3' block (rs7539542, rs10920531, and rs4950894) were all significantly associated with CAD (p=0.001 to 0.01). A similar trend, although not significant, was found in Italian subjects. Haplotype analysis of the combined populations revealed different haplotype distributions in cases and controls (p=0.0002), with one common haplotype being associated in homozygotes with a greater than three-fold increase in cardiovascular risk (OR=3.6, 95% CI 1.8-7.2). Some of the genotypes associated with increased cardiovascular risk were associated with 30-40% lower ADIPOR1 mRNA levels in blood mononuclear cells (n=60) and adipose tissue biopsies (n=28) (p=0.001 to 0.014). These findings point to genetic variability at the ADIPOR1 locus as a strong determinant of CAD susceptibility in type 2 diabetes.

Accordingly, in one aspect, the invention features methods for evaluating a subject, e.g., a human, e.g., a male human, e.g., a subject who has or is at risk for type 2 diabetes, to determine the subject's risk of developing cardiovascular disease. The methods include determining whether the subject has a polymorphism, e.g., detecting the presence or absence of a polymorphism, e.g., a single nucleotide polymorphism (SNP), in an adiponectin receptor 1 (ADIPOR1) gene of the subject. In some embodiments, the methods include determining whether the subject has, in one or both alleles of an ADIPOR1 gene of the subject, a polymorphism, e.g., a SNP, in a nucleotide corresponding to SNPs rs7539542 (also known as rs1139646), rs10920531, and/or rs4950894, or another SNP in linkage disequilibrium with one or more of these. The presence or absence of such a polymorphism is correlated with risk of cardiovascular disease. As used herein, "correlated with" means that that there is a statistically significant association between the polymorphism and risk of cardiovascular disease. The methods can include identifying the polymorphism as a risk or diagnostic factor for cardiovascular disease, e.g., by providing information, e.g., print material or computer readable medium, e.g., an informational, diagnostic, marketing or instructional print material or computer readable medium, e.g., to the subject or to a health care provider, identifying the polymorphism as a risk or diagnostic factor for cardiovascular disease. The methods can also include providing the subject with treatment and prevention options, e.g., alterations in diet, exercise, and smoking habits, e.g., to reduce non-genetic risk factors for cardiovascular disease, and/or prescribing a pharmaceutical agent for the treatment or prevention of cardiovascular disease.

In some embodiments, the presence, in one or both alleles of an ADIPOR1 gene of a subject, of a polymorphism that is in a nucleotide corresponding to SNP rs7539542, rs10920531, rs4950894, or another SNP in linkage disequilibrium with one or more of these is correlated with an increased risk for cardiovascular disease, e.g., in Type 2 diabetics. Generally, the presence of a polymorphism in linkage disequilibrium with a guanine (G) at the nucleotide corresponding to SNP rs7539542, an adenine (A) at the nucleotide corresponding to SNP rs10920531, or an adenine (A) at the nucleotide corresponding to rs4950894, in one or both alleles of the ADIPOR1 gene of the subject, is correlated with an increased risk of developing cardiovascular disease as compared to a reference value, e.g., a value for the comparable risk for a subject not having the polymorphism.

In some embodiments, determining whether the subject has a polymorphism can include: (i) providing a probe or primer, e.g., a labeled probe or primer, that includes a region of nucleotide sequence that hybridizes to a sense or antisense sequence from an ADIPOR1 gene or naturally occurring mutants thereof, or to the 5' or 3' flanking sequences naturally associated with an ADIPOR1 gene; (ii) exposing the probe/primer to nucleic acid of the subject; and (iii) detecting, e.g., by hybridization, e.g., in situ hybridization to the nucleic acid, or by amplification of the nucleic acid, the presence or absence of the polymorphism, e.g., a polymorphism in one or more of the nucleotides corresponding to SNPs rs7539542, rs10920531, and rs4950894 or another SNP in linkage disequilibrium with one or more of these.

In some embodiments, determining includes providing or obtaining a biological sample from the subject comprising an ADIPOR1 gene or fragment thereof, and detecting whether the subject has a polymorphism described herein. The detection can be performed, for example, by one or more of: chain terminating sequencing, restriction digestion, allele-specific polymerase reaction, single-stranded conformational polymorphism analysis, genetic bit analysis, temperature gradient gel electrophoresis, ligase chain reaction, or ligase/polymerase genetic bit analysis, allele specific hybridization, size analysis, nucleotide sequencing, 5' nuclease digestion, primer specific extension, and oligonucleotide ligation assay.

In some embodiments, the methods include diagnosing a subject as being at risk for or having a cardiovascular disease described herein. In some embodiments, the methods include performing a second diagnostic test, e.g., evaluating one or more of: insulin metabolism, plasma glucose levels, plasma lipid levels, urine protein levels, and glomerular filtration rate.

The subject is typically a human, e.g., a human with one or more other risk factors for cardiovascular diseases, e.g., a family history of cardiovascular disease or diabetes. In some embodiments, the subject has a family history of cardiovascular disease, or has an elevated level of a marker of cardiovascular disease, e.g., C reactive protein (CRP). In some embodiments, the subject has diabetes, e.g., type 2 diabetes. In some embodiments, the subject is Caucasian. In some embodiments, the subject is not Caucasian. In some embodiments, the subject is of European ancestry, e.g., Western European ancestry. The biological sample can include a cell sample, tissue sample, or at least partially isolated molecules, e.g., nucleic acids, e.g., genomic DNA, cDNA, mRNA, and/or proteins derived from the subject. The ADIPOR1 gene is ubiquitously expressed; expression is especially strong in skeletal muscle, so skeletal muscle cells can be used where protein levels are to be determined.

In another aspect, the invention features methods for evaluating a subject, e.g., a human, e.g., a male human, by determining a subject's risk of developing cardiovascular disease. The methods include determining, for one or both alleles of an ADIPOR1 gene of the subject, the identity of one or more of the nucleotides corresponding to SNPs rs7539542, rs10920531, rs4950894, or another SNP in linkage disequilibrium with one or more of these. In some embodiments, the methods include determining, for one or both alleles of an ADIPOR1 gene of the subject, the identity of one of more of the nucleotides corresponding to SNPs rs7539542, rs10920531, and rs4950894. A guanine (G) at the nucleotide corresponding to SNP rs7539542, an adenine (A) at the nucleotide corresponding to SNP rs10920531, or an adenine (A) at the nucleotide corresponding to SNP rs4950894, in one or both alleles of the ADIPOR1 gene of the subject, is correlated with an increased risk of developing cardiovascular disease compared to a reference value, e.g., a value for the comparable risk for a subject carrying a different allele in one or both chromosomes at the positions corresponding to SNPs rs7539542, rs10920531, and/or rs4950894.

In some embodiments, determining the identity of a nucleotide can include: (i) providing an oligonucleotide, e.g., a labeled oligonucleotide, that spans a nucleotide corresponding to SNPs rs7539542, rs10920531, rs4950894, or another SNP in linkage disequilibrium with one or more of these, (ii) exposing the oligonucleotide to nucleic acid of the subject; and/or (iii) detecting, e.g., by hybridization, e.g., in situ hybridization to the nucleic acid, or by amplification of the nucleic acid, the presence or absence of the nucleotide, e.g., a nucleotide corresponding to SNPs rs7539542, rs10920531, rs4950894, or another SNP in linkage disequilibrium with one or more of these.

In some embodiments, the methods include performing one or more of the following determinations, for one or both chromosomes of the subject:

(a) determining the identity of the nucleotide of the ADIPOR1 gene corresponding to SNP rs7539542, e.g., determining if the coding or non coding strand of an ADIPOR1 gene of the subject includes a G at the nucleotide corresponding to SNP rs7539542;

(b) determining the identity of the nucleotide of the ADIPOR1 gene corresponding to SNP rs10920531, e.g., determining if the coding or non coding strand of an ADIPOR1 gene of the subject includes an A at the nucleotide corresponding to SNP rs10920531; and/or (c) determining the identity of the nucleotide of the ADIPOR1 gene corresponding to SNP rs4950894, e.g., determining if the coding or non coding strand of an ADIPOR1 gene of the subject includes an A at the nucleotide corresponding to SNP rs4950894.

The presence of a G at SNP rs7539542, an A at SNP rs10920531, and/or an A at SNP rs4950894, are associated with increased risk of cardiovascular disease. The presence of a G at SNP rs4950894 is associated with protection, i.e., decreased risk of cardiovascular disease.

In some embodiments, the determining step includes amplifying at least a portion of an ADIPOR1 nucleic acid molecule of the subject, e.g., a portion including a nucleotide corresponding to SNPs rs7539542, rs10920531, rs4950894, or another SNP in linkage disequilibrium with one or more of these.

In some embodiments, the determining step includes sequencing at least a portion of an ADIPOR1 nucleic acid molecule of the subject, e.g., one or more portions including one or more nucleotides corresponding to SNPs rs7539542, rs10920531, rs4950894, or another SNP in linkage disequilibrium with one or more of these.

In some embodiments, the determining step includes hybridizing an ADIPOR1 nucleic acid molecule of the subject with a probe or primer, e.g., a probe or primer described herein, e.g., a probe or primer including a nucleotide corresponding to SNPs rs7539542, rs10920531, rs4950894, or another SNP in linkage disequilibrium with one or more of these.

In some embodiments, the method includes generating a dataset of the result of the determination, e.g., generating a print or computer readable material, e.g., an informational, diagnostic, marketing or instructional print material or computer readable medium, e.g., correlating the result of the determination with the subject's risk of developing cardiovascular disease. In some embodiments, the methods include providing the data to the subject or to a health care provider.

In another aspect, the invention features kits that include at least one probe or primer described herein, and instructions for using the kit to evaluate risk for cardiovascular disease in a subject. The kit can be used, e.g., by a subject or health care provider.

In another aspect, the invention provides computer readable records encoded with at least (a) a subject identifier, e.g., a patient identifier, (b) one or more results from an evaluation of the subject, e.g., a diagnostic evaluation described herein, e.g., the presence or absence of a polymorphism described herein in an ADIPOR1 gene of the subject, and optionally (c) a value for or related to a disease state, e.g., a value correlated with disease status or risk with regard to cardiovascular disease, e.g., a reference value. In some embodiments, the invention features a computer medium having a plurality of digitally encoded data records. Each data record includes a value representing the presence or absence of a polymorphism described herein in a biological sample, and/or a descriptor of the sample. The descriptor of the sample can be an identifier of the sample, a subject from which the sample was derived (e.g., a patient), a diagnosis, or a treatment (e.g., a preferred treatment). The data record can be structured as a table, e.g., a table that is part of a database such as a relational database (e.g., a SQL database of the Oracle or Sybase database environments). The invention also includes methods for communicating information about a subject, e.g., by transmitting information, e.g., transmitting a computer readable record as described herein, e.g., over a computer network.

In another aspect, the methods described herein can include determining a level of ADIPOR1 mRNA or protein, as an alternative or in addition to detecting a SNP as described herein. For example, those subjects who have a decreased level of ADIPOR1 mRNA or protein, e.g., as compared to a reference level, e.g., a control who has normal levels of ADIPOR1 mRNA or protein, can be considered to have an increased risk of developing cardiovascular disease. Such methods generally include obtaining a sample from a subject, i.e., a sample including nucleated cells or nucleic acids therefrom, e.g., RNA or genomic DNA, and determining a level of ADIPOR1 mRNA or protein in the sample. The ADIPOR1 gene is ubiquitously expressed; expression is especially strong in skeletal muscle, so skeletal muscle cells can be used where protein levels are to be determined. The level can be compared to a reference. A decreased level of ADIPOR1 mRNA or protein, e.g., as compared to a reference, indicates that the subject has an increased risk of cardiovascular disease.

In one aspect, the invention includes methods of evaluating a subject for risk of developing cardiovascular disease. The methods include obtaining a sample comprising cells from a subject, e.g., peripheral blood mononuclear cells (PBMC) or skeletal muscle cells; detecting a level of ADIPOR1 mRNA or protein in the sample; and comparing the level of ADIPOR1 mRNA or protein in the sample with a reference. The level of ADIPOR1 mRNA or protein in the sample as compare toe the reference indicates the subject's risk for cardiovascular disease.

In some embodiments, the reference represents a level of ADIPOR1 mRNA or protein in a normal subject. In general, the presence of a level of ADIPOR1 mRNA or protein that is below the level of ADIPOR1 mRNA or protein in the reference indicates that the subject has an increased risk of cardiovascular disease.

As used herein, the term "cardiovascular disease" refers to disorders in any of the various parts of the cardiovascular system, including, but not limited to, coronary artery disease (CAD), coronary heart disease, cardiomyopathy, valvular heart disease, ischemic heart disease, arteriosclerosis, ischemic stroke, hemorrhagic stroke, aneurysm, atherosclerosis, angina, pericardial disease (e.g., pericarditis, pericardial effusion, and constrictive pericarditis), vasculitis, and myocardial infarction. In some embodiments, the cardiovascular disease is CAD.

As used herein, the term "primer" refers to a single-stranded oligonucleotide that bind in a sequence-specific manner to a complementary strand of nucleic acid and act as a point of initiation of template-directed DNA synthesis under appropriate conditions. Such conditions can include, e.g., the presence of four different nucleoside triphosphates and an agent for polymerization, such as DNA or RNA polymerase or reverse transcriptase, an appropriate buffer, and a suitable temperature. The appropriate length of a primer depends on the intended use of the primer, but typically ranges from 10 to 50, e.g., 15 to 30, nucleotides. For example, primers can be 10, 12, 14, 16, 18, 20, 22, 24, 25, 26, 28 or 30 nucleotides in length. Short primer molecules generally require cooler temperatures to form sufficiently stable hybrid complexes with the template. A primer need not necessarily reflect the exact sequence of the template, but must be sufficiently complementary to hybridize with a template. The term "primer pair" refers to a set of primers including a 5' (upstream) primer that hybridizes with the 5' end of the DNA sequence to be amplified and a 3' (downstream) primer that hybridizes with the complement of the 3' end of the sequence to be amplified. In some embodiments, the primer binds to all or a part of SEQ ID NO:1, 2, or 3, e.g., a part including, e.g., spanning or termination at, a polymorphism as described herein.

As used herein, "hybridization probes" are oligonucleotides of between 5 and 1000 nucleotides that bind in a sequence-specific manner to a complementary strand of nucleic acid. Such probes can include peptide nucleic acids, as described, e.g., in Nielsen et al., Science, 254:1497-1500 (1991). The most appropriate length of the probe may vary depending upon the hybridization method in which it is being used. For example, particular lengths may be more appropriate for use in microfabricated arrays, while other lengths may be more suitable for use in classical hybridization methods. Such optimizations are known to the skilled artisan. For many purposes, suitable probes can range from about 5 to 100, e.g., 5 to 50, or about 5 to about 30 nucleotides in length. For example, probes can be 5, 6, 8, 10, 12, 14, 16, 18, 20, 22, 24, 25, 26, 28 or 30 nucleotides in length. The probe preferably overlaps at least one polymorphism described herein. The nucleotide sequence can correspond to the coding sequence of the allele or to the complement of the coding sequence of the allele. In some embodiments, the probe binds to all or a part of SEQ ID NO:1, 2, or 3, e.g., a part including, e.g., spanning or termination at, a polymorphism as described herein.

The terms "probe site" or "primer site" refer to the area of the target DNA to which a probe or primer hybridizes (binds).

As used herein, the term "spanning" means including at least four nucleotides immediately surrounding a reference nucleotide position. The at least four nucleotides can be immediately 5' and/or 3' to the reference nucleotide position.

The term "haplotype" is a set of closely linked alleles (genes or DNA polymorphisms) inherited as a unit. Different combinations of alleles are known as haplotypes. The term "allele" refers to one of the different forms of a gene, DNA sequence, or polymorphism, that can exist at a single locus.

As used herein, the process of "detecting" alleles or polymorphisms is variously described as "genotyping," "determining," or "identifying" an allele or polymorphism, or any similar phrase. The allele actually detected might be a disease-causing mutation, or a mutation that is in linkage disequilibrium with a disease-causing mutation. It will be manifest in the genomic DNA of a patient, but may also be detectable from RNA or protein sequences transcribed or translated from this region.

By "propensity," "predisposition," "susceptibility," or "risk" for disease is meant that certain alleles are statistically associated with a disease, as described herein. They are thus over-represented in frequency in individuals with disease as compared to healthy individuals.

As used herein, "linkage disequilibrium" means that genes, alleles, loci and/or genetic markers occur together in the population more frequently than expected on the basis of chance alone. This phenomenon is due to the tendency of genes, alleles, loci and/or genetic markers located on the same chromosome to be inherited together. Linkage disequilibrium can be measured by comparing the population frequency of a combination of genes, alleles, loci and/or genetic markers to the frequency expected on the basis of chance. Additional details regarding linkage analysis are included hereinbelow.

The term "polymorphism," as used herein, refers to the occurrence of two or more genetically determined alternative sequences or alleles in a population. The polymorphisms can be those variations (DNA sequence differences) that are generally round between individuals or different ethnic groups and/or geographic locations that, while having a different sequence, produce structurally or functionally equivalent gene products. The term can also refer to variants in the sequence that can lead to gene products that are not structurally or functionally equivalent. Polymorphisms also encompass variations that can be classified as alleles and/or mutations that can produce gene products that may have an altered function. Polymorphisms also encompass variations that can be classified as alleles and/or mutations that either produce no gene product or an inactive gene product or an active gene product produced at an abnormal rate or in an inappropriate tissue or in response to an inappropriate stimulus.

A "polymorphic marker" or "site" is the locus at which divergence occurs. Preferred markers have at least two alleles, each occurring at frequency of greater than 1%, and more preferably greater than 10% or 20% of a selected population. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic or biallelic polymorphism has two forms. A triallelic polymorphism has three forms.

A "single nucleotide polymorphism" is a polymorphism that occurs at a polymorphic site occupied by a single nucleotide. The site is usually preceded by and/or followed by highly conserved sequences of the allele (e.g., sequences that vary in less than $1/100$ or $1/1000$ members of the populations). A single nucleotide polymorphism usually arises due to substitution of one nucleotide for another at the polymorphic site. A "transition" is the replacement of one purine by another purine or one pyrimidine by another pyrimidine. A "transversion" is the replacement of a purine by a pyrimidine or vice versa. Single nucleotide polymorphisms can also arise from a deletion of a nucleotide or an insertion of a nucleotide relative to a reference allele. Typically the polymorphic site is occupied by a base other than the reference base. For example, where the reference allele contains the base "T" at the polymorphic site, the altered allele can contain a "C," "G," or "A" at the polymorphic site.

The term "isolated" is used herein to indicate that the material in question exists in a physical milieu distinct from that in which it occurs in nature. For example, an isolated nucleic acid of the invention is substantially isolated with respect to the complex cellular milieu in which it naturally occurs. In some instances, the isolated material will form part of a composition (for example, a crude extract containing other substances), buffer system or reagent mix. In other circumstance, the material can be purified to essential homogeneity, for example as determined by PAGE or column chromatography such as HPLC. Preferably, an isolated nucleic acid comprises at least about 50, 80 or 90 percent (on a molar basis) of all macromolecular species present.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1A:
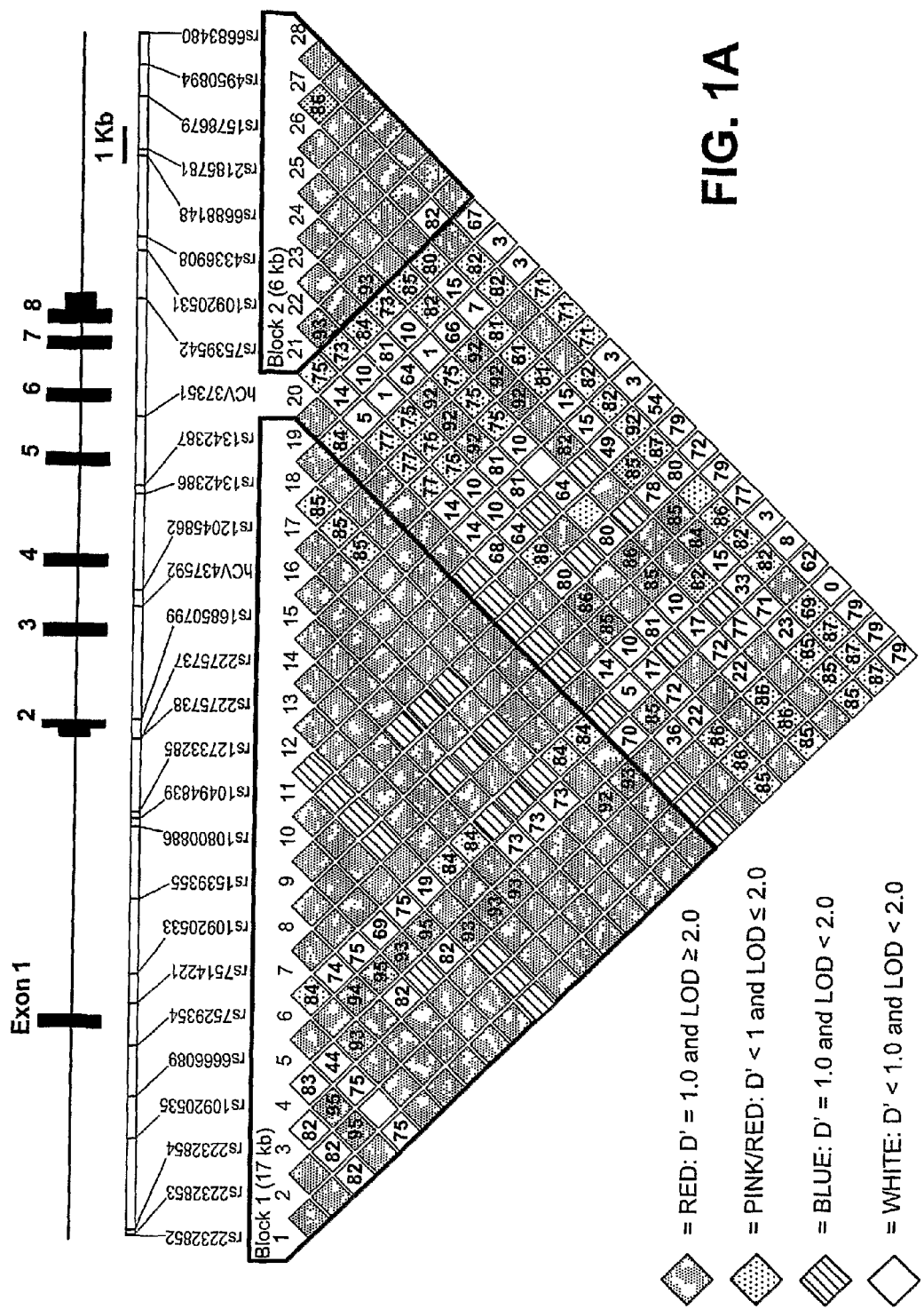
FIG. 1A is a Haploview plot of pairwise D'. Bright red indicates D'=1.0 and LOD≧2.0, shades of pink/red indicate D'<1 and LOD≦2.0, blue indicates D'=1.0 and LOD<2.0, white indicates D'<1.0 and LOD<2.0. Linkage disequilibrium blocks (indicated by the black line) were determined according to the confidence interval method using the Gabriel criteria (Gabriel et al., Science 296:2225-2229, 2002).

The invention is based, at least in part, on the inventors' discovery that certain polymorphisms and/or haplotypes within the adiponectin receptor 1 (ADIPOR1) gene correlate with increased risk of cardiovascular disease in Type 2 diabetics.

The diagnostic methods described herein can identify subjects having, or at risk of developing, cardiovascular disease, e.g., coronary artery disease (CAD), ischemic heart disease, atherosclerosis, angina, and myocardial infarction. The prognostic assays described herein can be used to determine whether a subject should be treated for, e.g., administered an agent to treat or prevent, cardiovascular disease.

The findings described herein suggest that sequence variants in the 3' region of the ADIPOR1 gene are significant determinants of cardiovascular risk in type 2 diabetes. This effect appears to be due to allelic differences in ADIPOR1 expression, which may influence the anti-atherogenic effects of adiponectin on target tissues. These results confirm and extend the evidence implicating adiponectin as a physiological modulator of atherogenesis and point to variability in the ADIPOR1 gene as a key regulator of this effect.

Several features of these findings make the possibility of a false positive result unlikely. First, the evidence of association with CAD was highly significant, with Bonferroni-adjusted p values ranging from 0.005 to 0.036 and False Discovery Rates ranging from 0.005 to 0.012. Second, there were no major differences in allelic frequencies among European populations that would explain these findings on the basis of population stratification. Third, the association with CAD, although with different strength, was observed in two distinct Caucasian populations recruited at different centers, one in Boston, and the other in Italy. Fourth, some of the genotypes associated with CAD also showed an association with decreased mRNA levels in two different cell types, providing a plausible biological basis for the case-control results.

In the Italian study, the association with CAD was significant for only one SNP and only for the contrast between minor and major allele homozygotes. The fact that the ORs at this and other polymorphic loci were not significantly different in the two populations is reassuring, since it suggests that the estimates obtained in the two studies are different measures of the same genetic effect. Nonetheless, the results in the Italian population cannot be formally considered as a replication of those in Boston.

A recent study in non-diabetic Mexican Americans has described a strong, positive correlation between ADIPOR1 expression levels in skeletal muscle and insulin-sensitivity as determined by the glucose clamp (Civitarese et al., *Diabetologia*. 47:816-820, 2004). In addition, a recent report from Germany has described an association between insulin-resistance, as determined by OGTT and the glucose clamp, and ADIPOR1 polymorphisms in the 5' part of the gene (Stefan et al., *Diabetologia*. 48:2282-2291, 2005). The 3' flanking region of the gene, which as described herein is associated with CAD, was not investigated in that report.

ADIPOR1 polymorphisms may also affect cardiovascular risk through mechanisms that are independent of insulin-sensitivity. In cultured cells, adiponectin suppresses monocyte adhesion to the endothelium, inhibit smooth muscle cell proliferation, and reduce foam cell formation (Ouchi et al, Circulation 100:2473-2476, 1999, Ouchi et al., Circulation 103:1057-1063, 2001, and Arita et al., Circulation 105:2893-2898, 2002). Administration of recombinant adenovirus expressing human adiponectin to apoE deficient animals causes a 30% reduction in the formation of atherosclerotic lesions in the absence of any effects on metabolic traits (Okamoto et al., Circulation 106:2767-2770, 2002, Yamauchi et al., J Biol Chem 278:2461-2468, 2003). In humans, high adiponectin levels have a protective effect on cardiovascular events that is independent of other cardiovascular risk factors and systemic inflammation markers (Pischon et al., JAMA 291:1730-1737, 2004, Schulze et al., Diabetes 54:534-539, 2005). The decrease in ADIPOR1 expression associated with the ADIPOR1 SNPs in the 3' block may impair such direct anti-atherogenic actions of adiponectin. The fact that the association between ADIPOR1 SNPs and gene expression was detected in circulating monocytes—the precursors of foam cells in atherosclerotic plaques—makes this hypothesis especially attractive.

While the effect of ADIPOR1 variability on CAD risk appears to be mediated by differences in gene expression, the identities of the sequence variants that are responsible for this effect are unknown. The observation that the four haplotypes fall into more than two risk classes suggests the involvement of multiple polymorphisms—either the tagging SNPs or variants in linkage disequilibrium with them—interacting with each other.

ADIPOR1 SNPs Associated with CVD

Three SNPs have been identified in particular that are associated with an increased risk of cardiovascular disease, rs4950894, rs7539542, and rs10920531.

SNP rs7539542

The sequence of the genome that includes SNP rs7539542 is as follows:

```
                                              (SEQ ID NO: 2)
AAAAAGTAAA GCTGTATTGG GGAATGGATG CTAGGAATTC

AATTAGGTCC ATTTATTGGC CTGCATGTGC CAGCCTGTCA

ATGCCTATGA TTCAAATTTG TGCCTCAGGA GAATCTGAAA

TTATCACAGG TCTTACTTAA TGTTTTGGAG TTGTGTGCAA

ATAATCAAGA CCATACATGT GAAATCTTTG AATGCCAAGT S

TCTTCTGTAC TTTCTTTTAT TAACATCATA GTCTTTGCAT

CAAGATACAT AGCAATGATA GCAGGTTTCT TTTTAAAGCT

TAGTATTAAA TATTAAATAT CTTTCCCCAT TTAAATTTTA

CATTACTCTG CCAAGAAAAA AAAAAAATTA AAACTCAAGT

TACTTGAAGC CTGGACACAC TTCCATGATT AGCCGGGCTA
```

The position of SNP rs7539542 is shown as a bold S. The major variant is a C, the minor variant is a G. Note that rs7539542 is also known as rs1139646. The presence of the minor variant in either or both alleles is associated with increased risk of cardiovascular disease.

SNP rs10920531

The sequence of the genome that includes SNP rs10920531 is as follows:

```
                                              (SEQ ID NO: 3)
AACATTTTGC TACTACAAAC AGCTGCAATG AACCCTTTGG

TACAAGCCAG GTTTTTCCAA GAGCGGTGTG TTTGAAAGCG

TGAGTAGCGA CCCATTACTG AGTCATGAGA ACAATTTAGT

GGGTCAGCCA GCACTGTTTT TAAGTGAAGT AACCTAGGTT

AGATATCAGA TGCATTTCAT ATTGTATAGT GTCATTTCAC

GAAATGTTTG AATGTTGTCA ACATGTATAC ACTCTTTGTG

TGTCCATGTA AAGTGGTCCT GCAATGTATA CTTCCACCAG

CAGCATCTGG TCTGCTCTAC ATCTGCACCA ACACTCAATA

TTAGGCTTCT AATTTGGTTT CAGTCTGGTT GGAGTAAGAC

AGATTATCAT TTTGGTTTTA ATTTACATTT CCTTGGTTAC

TTGAGGCAGA GAAACTTTTC CTGTTGGTGT AGGTGGATTA

TTTTTTTAAA AGGATAATTT GTTCTTCCAT TGTAGAAACT
```

-continued

```
TGACTCTTGA CATGAACCCA M CTTTAACTCA AAAAGACTGC

CCTTAAACTG CCTGCATTAG CTGAGAAGTG ATTACTGATA

TCTTGCGCTA TATAATGAAC AGAACTCATG TCAGGTTGAG

TACAATTCAC AATAGCACCG AAAAGCATGG AATGACCCCT

GGATGAGACA ACCTTAGGCA ACATGGGATA TATCCCTAAA

CTTTGGGATG TATTCCAACA
```

The position of SNP rs10920531 is shown as a bold M. The major variant is a C, the minor variant is an A. The presence of the minor variant in either or both alleles is associated with increased risk of cardiovascular disease.

SNP rs4950894

The sequence of the genome that includes SNP rs4950894 is as follows:

```
                                          (SEQ ID NO: 1)
TAGTGCAGA TTAAGTGCAA TGTTTCTTTG TTGATAGTTG

ATATTCTGTC TGGGAGATCT GTCCAGTGCT GAAAGCGGAG

TGTTGAAGTC TTCAGGTATT ATTGTGTTGG GGCCTATCTC

TGTCTGTAGC TCTAATAATA TTTGCTTTAT ATACCTGGGT

GCTTCAGTGT TAGATGCATA TATGTTTACA AGCGTTATAT

CCTCTTGCTG AATTGTCCCG TTTATCACTA TATAATGATC

TCTTTGTCT CTTCTTGTTT TTGTCTTAAA ATCTATTTTC

CTTTACATAT AAGCATTTCC CCTAATAAAA TCTTTGCACA

TATAATTTCA TCTTAGCAAG TGCTTTCCTG AGAACTAGAC

TAACACACAG GACATCTGAG AATTTCTTTG GGTCCTATTC

ATTTGCAATA ATCCAAGTTT ACTAAAGTTC CCAAAGTTGC

ATTTTTTAAA AATTGAAAAT GGGTGTTGTA TTAGTCTGTT

CTCTCACTGC TAACAAAGAT R TATCCCAGAC TGGATAATTT

ATAAAGGAAA AAGGTGTGGT TTTTTTTTTT TTTTGAGATG

GAATCTTACT CTGTTGACCA GGCTGGAGTG CAGTGGTGCA

ATCTCTGCTT GCTGCAACCT CCACCTCCCA GGTTCAAGCA

ATTCTCCTGC CTCATCCTCC CAAGTAGCTG GGATTACAGG

CATGAGCCAC CATGCCTGGC TGGTTTTTGT TTGTTTGTTT

GAGACGGAGT CTCACTCTGT CGCCCAGGTT GGAGTGCAGT

GGTGTAATCT TGGCTCACTG CAACCTCTGA CTCCCAGGTT

CAAGTGATTC TTGTGACTCA CCCTCCTGAG TAGCTGGGAT

TACAGGTCTC TGCCACCACA CCCGGCTAAT TTTTTTGTGT

TTTTAGTAGA GGTGGGGTTT CAGCATGTTG GCCAGGCTGG

TACTGAACTC CTGACCTCAA GTGATCTGCC TGCCTCGGCC

TCCCAAAGTG CTGGGATTAT AGGCATAAGC CACCATGCCC
```

The position of SNP rs4950894 is shown as a bold R. The major variant is a A, the minor variant is an G. The presence of the major variant in either or both alleles is associated with increased risk of cardiovascular disease.

Diagnostic Assays

The diagnostic assays described herein generally involve evaluating genetic variability, e.g., the presence or absence of polymorphisms, within one or both alleles of an ADIPOR1 gene in a subject. Alternatively or in addition, the methods can include determining a level of ADIPOR1 mRNA or protein. Once the presence of a polymorphism associated with an increased risk of cardiovascular disease is confirmed, the methods can include treating the subject, e.g., to reduce other risk factors for cardiovascular disease, e.g., non-genetic risk factors such as smoking, obesity, poor or high fat diet, and lack of exercise. In some embodiments, the methods can include prescribing a medication that treats or prevents or delays the onset of cardiovascular disease.

Genotype Screening and Linkage Analysis

Genetic screening (also called genotyping or molecular screening), can be broadly defined as testing to determine if a patient has mutations, e.g., polymorphisms, that either cause a disease state or are "linked" to the mutation causing a disease state. Linkage refers to the phenomenon that DNA sequences that are close together in the genome have a tendency to be inherited together. Two sequences may be linked because of some selective advantage of co-inheritance. More typically, however, two polymorphic sequences are co-inherited because of the relative infrequency with which meiotic recombination events occur within the region between the two polymorphisms. The co-inherited polymorphic alleles are said to be in linkage disequilibrium with one another because, in a given human population, they tend to either occur together or else not occur at all in any particular member of the population. Indeed, where multiple polymorphisms in a given chromosomal region are found to be in linkage disequilibrium with one another, they define a quasi-stable genetic "haplotype." In contrast, recombination events occurring between two polymorphic loci cause them to become separated onto distinct homologous chromosomes. If meiotic recombination between two physically linked polymorphisms occurs frequently enough, the two polymorphisms will appear to segregate independently and are said to be in linkage equilibrium.

While the frequency of meiotic recombination between two markers is generally proportional to the physical distance between them on the chromosome, the occurrence of "hot spots" as well as regions of repressed chromosomal recombination can result in discrepancies between the physical and recombinational distance between two markers. Thus, in certain chromosomal regions, multiple polymorphic loci spanning a broad chromosomal domain may be in linkage disequilibrium with one another, and thereby define a broad-spanning genetic haplotype. Furthermore, where a disease-causing mutation is found within or in linkage with this haplotype, one or more polymorphic alleles of the haplotype can be used as a diagnostic or prognostic indicator of the likelihood of developing the disease. This association between otherwise benign polymorphisms and a disease-causing polymorphism occurs if the disease mutation arose in the recent past, so that sufficient time has not elapsed for equilibrium to be achieved through recombination events. Therefore, identification of a human haplotype that spans or is linked to a disease-causing mutational change serves as a predictive measure of an individual's likelihood of having inherited that disease causing, e.g., cardiovascular disease-causing, mutation. Importantly, such prognostic or diagnostic procedures can be utilized without necessitating the identification and isolation of the actual disease-causing lesion.

Indeed, the statistical correlation between a disorder and polymorphism does not necessarily indicate that the polymorphism directly causes the disorder. Rather the correlated polymorphism may be a benign allelic variant that is linked to (i.e. in linkage disequilibrium with) a disorder-causing mutation that has occurred in the recent human evolutionary past, so that sufficient time has not elapsed for equilibrium to be achieved through recombination events in the intervening chromosomal segment. Thus, for the purposes of diagnostic and prognostic assays for a particular disease, detection of a polymorphic allele associated with that disease can be utilized without consideration of whether the polymorphism is directly involved in the etiology of the disease. Furthermore, where a given benign polymorphic locus is in linkage disequilibrium with an apparent disease-causing polymorphic locus, still other polymorphic loci that are in linkage disequilibrium with the benign polymorphic locus are also likely to be in linkage disequilibrium with the disease-causing polymorphic locus. Thus these other polymorphic loci will also be prognostic or diagnostic of the likelihood of having inherited the disease-causing polymorphic locus. Indeed, a broad-spanning human haplotype (describing the typical pattern of co-inheritance of alleles of a set of linked polymorphic markers) can be targeted for diagnostic purposes once an association has been drawn between a particular disease or condition and a corresponding human haplotype. Thus, the determination of an individual's likelihood for developing a particular disease of condition can be made by characterizing one or more disease-associated polymorphic alleles (or even one or more disease-associated haplotypes) without necessarily determining or characterizing the causative genetic variation.

Linkage disequilibrium can be determined using routine methods, e.g., using the GOLD (Abecasis and Cookson, Bioinformatics, 16, 182-183, 2000) and Haploview (Barret et al., Bioinformatics, 21:263-265, 2005) software packages.

Methods of Detecting ADIPOR1 Polymorphisms

The methods described herein, e.g., diagnostic and prognostic methods described herein, can include detecting one or more ADIPOR1 polymorphisms. Methods described herein provide for determining whether a subject carries a polymorphism of the ADIPOR1 gene. For example, methods typically include determining which allele or alleles of the human ADIPOR1 gene a subject carries.

Biological Samples

Polymorphisms can be detected in a target nucleic acid from an individual being analyzed. For assay of genomic DNA, virtually any biological sample (other than pure red blood cells) is suitable. For example, convenient tissue samples include whole blood, semen, saliva, tears, urine, fecal material, sweat, buccal cells, skin and hair (e.g., follicles).

Amplification of DNA from target samples can be accomplished by methods known to those of skill in the art, e.g., polymerase chain reaction (PCR) (see, e.g., U.S. Pat. No. 4,683,202), ligase chain reaction (LCR) (Wu and Wallace, Genomics, 4:560 (1989); Landegren et al., Science, 241:1077 (1988)), transcription amplification (Kwoh et al., Proc. Natl. Acad. Sci. USA, 86:1173 (1989)), self-sustained sequence replication (Guatelli et al., Proc. Natl. Acad. Sci. USA, 87:1874 (1990)), and nucleic acid based sequence amplification (NASBA). A variety of suitable procedures that can be employed to detect polymorphisms are known in the art; exemplary methods are described in further detail herein. Examples of techniques for detecting point mutations include, but are not limited to, selective oligonucleotide hybridization, selective amplification, or selective primer extension (Saiki et al., Nature, 324:163-166(1986); Saiki et al., Proc. Natl. Acad. Sci. USA, 86:6230-6234 (1989)). See also U.S. Pat. No. 6,410,231; U.S. Pat. No. 6,361,947; U.S. Pat. No. 6,322,980; U.S. Pat. No. 6,316,196; and U.S. Pat. No. 6,258,539.

PCR/LCR

As one example, a polymorphism can be detected in a polymerase chain reaction (PCR), e.g., by anchor PCR or RACE PCR, or, alternatively, in a ligation chain reaction (LCR), the latter of which can be particularly useful for detecting point mutations in the ADIPOR1 gene. This method can include the steps of collecting a sample of cells from a subject, isolating nucleic acid (e.g., genomic, mRNA or both) from the sample, contacting the nucleic acid sample with one or more primers which specifically hybridize to an ADIPOR1 gene under conditions such that hybridization and amplification of the ADIPOR1 gene (if present) occurs, and detecting the presence or absence of an amplification product, or detecting the size of the amplification product and comparing the length to a control sample. PCR and/or LCR can be used as a preliminary amplification step in conjunction with any of the techniques used for detecting mutations described herein.

Allele-Specific Probes

The design and use of allele-specific probes for analyzing polymorphisms is known in the art (see, e.g., Dattagupta, EP 235,726; Saiki, WO 89/11548). Allele-specific probes can be designed to hybridize differentially, e.g., to hybridize to a segment of DNA from one individual but not to a corresponding segment from another individual, based on the presence of polymorphic forms of the segment. Relatively stringent hybridization conditions can be utilized to cause a significant difference in hybridization intensity between alleles, and possibly to obtain a condition wherein a probe hybridizes to only one of the alleles. High stringency conditions include TMAC (tetramethylammonium chloride), SDS, EDTA, Denhart's Solution, and yeast tRNA at 52° C. Probes can be designed to hybridize to a segment of DNA such that the polymorphic site aligns with a central position of the probe.

Allele-specific probes can be used in pairs, wherein one member of the pair matches perfectly to a reference form of a target sequence, and the other member of the pair matches perfectly to a variant of the target sequence. The use of several pairs of probes immobilized on the same support may allow simultaneous analysis of multiple polymorphisms within the same target sequence.

Arrays

In some embodiments, genetic mutations in ADIPOR1 can be identified by hybridizing a sample (and, optionally, control nucleic acids), e.g., DNA or RNA, to two-dimensional arrays, e.g., chip based arrays (see, e.g., WO 95/11995). Such arrays include a plurality of addresses, each of which is positionally distinguishable from the other. A different probe is located at each address of the plurality. A probe can be complementary to a region of an ADIPOR1 nucleic acid or a putative variant (e.g., allelic variant) thereof. A probe can have one or more mismatches to a region of an ADIPOR1 nucleic acid (e.g., a destabilizing mismatch). The arrays can have a high density of addresses, e.g., can contain hundreds or thousands of oligonucleotides probes (Cronin et al., Human Mutation, 7:244-255 (1996); Kozal et al., Nature Medicine, 2:753-759 (1996)). For example, genetic mutations in ADIPOR1 can be identified in two-dimensional arrays containing light-generated DNA probes as described in Cronin et al., supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific-mutations by using smaller, specialized probe arrays complementary to all variants or mutations detected. Each mutation array is composed of parallel probe sets, one complementary to the wild-type gene and the other complementary to the mutant gene.

WO 95/11995 also describes subarrays that are optimized for the detection of variant forms of a precharacterized polymorphism. Such a subarray contains probes designed to be complementary to a second reference sequence, which is an allelic variant of the first reference sequence. The second group of probes is designed to exhibit complementarity to the second reference sequence. The inclusion of a second group (or further groups) can be particularly useful for analyzing short subsequences of the primary reference sequence in which multiple mutations are expected to occur within a short distance commensurate with the length of the probes (e.g., two or more mutations within 9 to 21 bases).

Allele-Specific Primers

An allele-specific primer that hybridizes to a site on target DNA overlapping a polymorphism and only primes amplification of an allelic form to which the primer exhibits perfect complementarily can be used to detect polymorphisms. Oligonucleotides used as primers for specific amplification can carry the mutation of interest in the center of the molecule (so that amplification depends on differential hybridization) (Gibbs et al., Nucleic Acids Res., 17:2437-2448 (1989)), or at the extreme 3' end of one primer where, under appropriate conditions, mismatch can prevent, or reduce polymerase extension (Prosser, Trends Biotechnol., 11 (6):238-246 (1993)). In addition, it may be desirable to introduce a novel restriction site in the region of the mutation to facilitate cleavage-based detection (Gasparini et al., Mol. Cell Probes, 6:1-7 (1992)). It is anticipated that in certain embodiments amplification can also be performed using Taq ligase for amplification (Barany, Proc. Natl. Acad. Sci. USA, 88:189-193 (1991)). In such cases, ligation will occur only if there is a perfect match at the 3' end of the 5' sequence, making it possible to detect the presence of a known mutation at a specific site by looking for the presence or absence of amplification.

Such a primer can be used in conjunction with a second primer that hybridizes at a distal site. Amplification proceeds from the two primers leading to a detectable product signifying the particular allelic form is present. A control is usually performed with a second pair of primers, one of which shows a single base mismatch at the polymorphic site and the other of which exhibits perfect complementarily to a distal site. The single-base mismatch prevents amplification and no detectable product is formed. The method can be optimized by including the mismatch in the 3'-most position of the oligonucleotide aligned with the polymorphism because this position is most destabilizing to elongation from the primer. See, e.g., WO 93/22456.

A further method of detecting point mutations is the chemical ligation of oligonucleotides as described in Xu et al., Nature Biotechnol., 19:148-152 (2001). Adjacent oligonucleotides, one of which selectively anneals to the query site, are ligated together only if the nucleotide at the query site of the sample nucleic acid is complementary to the query oligonucleotide; ligation can be monitored, e.g., by fluorescent dyes coupled to the oligonucleotides.

Direct Sequencing

In some embodiments, any of a variety of sequencing reactions known in the art can be used to directly sequence the ADIPOR1 gene, thereby to detect mutations by comparing the sequence of the sample ADIPOR1 with the corresponding wild-type (control) sequence. For example, automated sequencing procedures can be utilized when performing a diagnostic assays (Naeve et al., Biotechniques, 19:448-453 (1995)), including sequencing by mass spectrometry.

The direct analysis of the sequence of polymorphisms of the present invention can be accomplished using, e.g., the dideoxy chain termination method or the Maxam Gilbert method (see, e.g., Sambrook et al., *Molecular Cloning: A Laboratory Manual*, 3d ed., 2001, Cold Spring Harbor, which is hereby incorporated in its entirety; Zyskind et al., *Recombinant DNA Laboratory Manual*, Acad. Press, 1988).

Single Base Extension

Polymorphisms described herein can also be detected using single base extension (SBE), a dideoxy chain termination sequencing procedure in which only the polymorphic site is sequenced, followed by fluorescence polarization (FP) analysis (e.g., using the AcycloPrime™-FP SNP Detection System, Perkin-Elmer). This assay is based on the principle that incorporation of a fluorescent terminator into a primer oligonucleotide increases its polarization (see, e.g., Hsu et al., Biotechniques, 31:560-570 (2001)). A nucleotide at a polymorphic site can be determined by using different fluorescent terminators in the SBE reactions. For example, SNP-containing PCR products can be amplified from study subjects in 96-well plates using primers described herein. After shrimp alkaline phosphatase treatment to inactivate unincorporated dNTPs and primers, PCR products can undergo SBE using a primer described herein and fluorescent terminators. Fluorescence polarization can be determined using, e.g., a Wallac VICTOR²™ Multilabel Plate Reader (Perkin-Elmer).

Denaturing Gradient Gel Electrophoresis

The movement of mutant or wild-type fragments in polyacrylamide gels containing a gradient of denaturant can be used to detect polymorphisms using denaturing gradient gel electrophoresis (DGGE) (Myers et al., Nature, 313:495-498 (1985)). When DGGE is used as the method of analysis, DNA can be modified to ensure that it does not completely denature, for example, by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum et al., Biophys. Chem., 26:235-246 (1987)).

Amplification products generated using the polymerase chain reaction can be analyzed, e.g., by the use of denaturing gradient gel electrophoresis. Different alleles can be identified based on the different sequence-dependent melting properties and electrophoretic migration of DNA in solution. See, e.g., Erlich, ed., *PCR Technology, Principles and Applications for DNA Amplification*, W.H. Freeman and Co, New York, 1992, Chapter 7.

Single-Strand Conformation Polymorphism Analysis

Other methods for detecting alterations in electrophoretic mobility can also be used to identify mutations in ADIPOR1 genes. For example, single strand conformation polymorphism (SSCP) can be used to detect differences in electrophoretic mobility between mutant and wild type nucleic acids by alteration in electrophoretic migration of single stranded PCR products (Orita et al., Proc. Natl. Acad. Sci. USA, 86:2766 (1989); see also Cotton, Mutat. Res., 285:125-144 (1993); and Hayashi, Genet. Anal. Tech. Appl., 9:73-79 (1992)). Single-stranded DNA fragments of sample and control ADIPOR1 nucleic acids are heated or otherwise denatured, to form single stranded amplification products, and subsequently allowed to renature (e.g., by cooling), forming secondary structures. The secondary structure of single-stranded nucleic acids varies according to sequence; the resulting alteration in electrophoretic mobility enables the detection of even a single base change. The DNA fragments can be labeled or detected with labeled probes. The sensitivity of the assay may be enhanced by using RNA (rather than DNA), in which the secondary structure is more sensitive to a change in sequence. In some embodiments, the subject method utilizes heteroduplex analysis to separate double stranded heteroduplex molecules on the basis of changes in electrophoretic mobility (Keen et al., Trends Genet., 7:5 (1991)).

Mismatch Detection/RNase Protection

Other methods for detecting mutations in the ADIPOR1 gene include methods in which protection from cleavage agents is used to detect mismatched bases in RNA/RNA or RNA/DNA heteroduplexes (Myers et al., Science, 230:1242-1246 (1985); Cotton et al., Proc. Natl. Acad. Sci. USA, 85:4397-4401 (1988); Saleeba et al., Methods Enzymol., 217:286-295 (1992)).

For example, the mismatch cleavage reaction can employ one or more proteins that recognize mismatched base pairs in double-stranded DNA (so called "DNA mismatch repair" enzymes) in defined systems for detecting and mapping point mutations in ADIPOR1 cDNAs obtained from samples of cells. For example, the mutY enzyme of *E. coli* cleaves A at G/A mismatches and the thymidine DNA glycosylase from HeLa cells cleaves T at G/T mismatches (Hsu et al., Carcinogenesis, 15:1657-1662 (1994); U.S. Pat. No. 5,459,039).

Detection of Additional Polymorphisms

Alterations or mutations in an ADIPOR1 gene can be identified by a number of methods known in the art, to thereby identify other, additional polymorphisms that may be associated with susceptibility for cardiovascular disease. In some embodiments, the methods include detecting, in a sample from the subject, the presence or absence of a genetic alteration characterized by an alteration affecting the integrity of a gene encoding an ADIPOR1 protein, or the mis-expression of the ADIPOR1 gene. For example, such genetic alterations can be detected by ascertaining the existence of at least one of 1) a deletion of one or more nucleotides from an ADIPOR1 gene; 2) an addition of one or more nucleotides to an ADIPOR1 gene; 3) a substitution of one or more nucleotides of an ADIPOR1 gene, 4) a chromosomal rearrangement of an ADIPOR1 gene; 5) an alteration in the level of a messenger RNA transcript of an ADIPOR1 gene; 6) aberrant modification of an ADIPOR1 gene, such as of the methylation pattern of the genomic DNA; 7) the presence of a non-wild type splicing pattern of a messenger RNA transcript of an ADIPOR1 gene; and 8) allelic loss of an ADIPOR1 gene. Methods are known in the art and described herein for detecting such genetic alterations. Once additional alterations are identified, one of skill in the art would be able to determine whether they are in linkage disequilibrium with a polymorphism described herein.

Expression Monitoring and Profiling

In some embodiments, the methods described herein include determining the presence, level, or absence of ADIPOR1 protein or nucleic acid in a biological sample. This can be achieved by methods known in the art, which generally include obtaining a biological sample from a test subject and contacting the biological sample with a compound or an agent capable of detecting the protein or nucleic acid (e.g., mRNA, genomic DNA) that encodes ADIPOR1 such that the presence of the protein or nucleic acid is detected in the biological sample. The level of expression of ADIPOR1 can be measured in a number of ways, including, but not limited to: measuring the mRNA encoded by the ADIPOR1 gene; measuring the amount of protein encoded by ADIPOR1; or measuring the activity of the protein encoded by the gene.

The level of mRNA corresponding to ADIPOR1 in a cell can be determined both by in situ and by in vitro methods.

Isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length nucleic acid, or a portion thereof, such as an oligonucleotide of at least 7, 15, 30, 50, 100, 250 or 500 nucleotides in length and sufficient to specifically hybridize to mRNA or genomic DNA of ADIPOR1 (e.g., to regions of SEQ ID NOs:1, 2, or 3 that include SNPs rs4950894, rs7539542, or rs10920531 and is present in the mRNA). A probe that "specifically" hybridizes is one that will hybridize, under sufficiently stringent conditions, to one variant of a polymorphic sequence, but not another. The probe can be disposed on an address of an array, e.g., an array described herein. Suitable probes for use in diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described herein. A skilled artisan can adapt known mRNA detection methods for use in detecting the level of mRNA encoded by the gene.

The level of mRNA in a sample that is encoded by a gene can be evaluated with nucleic acid amplification, e.g., by rtPCR (Mullis, U.S. Pat. No. 4,683,202), ligase chain reaction (Barany, supra), self sustained sequence replication (Guatelli et al., Proc. Natl. Acad. Sci. USA, 87:1874-1878 (1990)), transcriptional amplification system (Kwoh et al., Proc. Natl. Acad. Sci. USA, 86:1173-1177 (1989)), Q-Beta Replicase (Lizardi et al., Bio/Technology, 6:1197 (1988)), rolling circle replication (Lizardi et al., U.S. Pat. No. 5,854,033), or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the gene being analyzed.

In another embodiment, the methods further include contacting a control sample with a compound or agent capable of detecting mRNA, or genomic DNA, and comparing the presence of the mRNA or genomic DNA in the control sample with the presence of ADIPOR1 mRNA or genomic DNA in the test sample. In still another embodiment, serial analysis of gene expression (as described in, e.g., U.S. Pat. No. 5,695,937) is used to detect transcript levels of ADIPOR1.

A variety of methods can be used to determine the level of ADIPOR1 protein. In general, these methods include contacting an agent that selectively binds to the protein, such as an antibody, with a sample to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect ADIPOR1 in a biological sample in vitro as well as in vivo. In vitro techniques for detection include enzyme linked immunosorbent assays (ELISAs), immunoprecipitations, immunofluorescence, enzyme immunoassay (EIA), radioimmunoassay (RIA), and Western blot analysis. In vivo techniques for detection of ADIPOR1 include introducing into a subject a labeled antibody. For example, the antibody can be labeled with a radioactive marker whose presence and location in a subject can be detected by standard imaging techniques. In another embodiment, the sample is labeled, e.g., biotinylated, and then contacted to the antibody, e.g., an antibody positioned on an antibody array. The sample can be detected, e.g., with avidin coupled to a fluorescent label.

In another embodiment, the methods further include contacting the control sample with a compound or agent capable of detecting ADIPOR1, and comparing the presence of ADIPOR1 protein in the control sample with the presence of the protein in the test sample.

Kits

The invention also includes kits for detecting the presence of ADIPOR1 in a biological sample. For example, the kit can include a compound or agent capable of detecting ADIPOR1 protein (e.g., an antibody) or mRNA (e.g., a nucleic acid probe); and/or an agent useful to evaluate an ADIPOR1 polymorphism, e.g., a probe or primer described herein; and a standard. The compound or agent can be packaged in a suitable container. The kit can further include instructions for using the kit to evaluate a subject, e.g., for risk of cardiovascular disease.

The kits generally include (a) the agent, e.g., an ADIPOR1 primer or probe, and (b) informational material. The informational material can be descriptive, instructional, marketing or other material that relates to the methods described herein and/or the use of the agent, e.g., an ADIPOR1 primer or probe, for the methods described herein. For example, the informational material relates to cardiovascular disease, e.g., to evaluation of risk for cardiovascular disease.

In one embodiment, the informational material can include instructions to use the agent in a suitable manner to perform the methods described herein, e.g., instructions to use the agent in polymerase chain reaction (PCR).

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about the agent and/or its use in the methods described herein. Of course, the informational material can also be provided in any combination of formats.

In addition to an agent used to evaluate an ADIPOR1 polymorphism, the composition of the kit can include other ingredients, such as a solvent or buffer, a stabilizer, or a preservative. Alternatively, the other ingredients can be included in the kit, but in different compositions or containers than the agent. In such embodiments, the kit can include instructions for admixing the agent and the other ingredients, or for using the agent together with the other ingredients.

The agent can be provided in any form, e.g., liquid, dried or lyophilized form. It is preferred that the agent be substantially pure and/or sterile. When the agent is provided in a liquid solution, the liquid solution preferably is an aqueous solution, with a sterile aqueous solution being preferred. When the agent is provided as a dried form, reconstitution generally is by the addition of a suitable solvent. The solvent, e.g., sterile water or buffer, can optionally be provided in the kit.

The kit can include one or more containers for the composition containing the agent. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit forms of the agent. For example, the kit includes a plurality of syringes, ampoules, foil packets, or blister packs, each containing a single unit form of the agent. The containers of the kits can be air tight and/or waterproof.

Diabetes Mellitus

In some embodiments, subjects as described herein have, or are at risk for, Type 2 diabetes mellitus (T2D). A diagnosis of T2D can be made, e.g., on the basis of symptom history confirmed by a fasting plasma glucose (FPG) level greater than 200 mg/dl. Other symptoms representative of T2D diabetes include polyuria, polydipsia, fatigue, blurred vision, and glucosuria.

Subjects who are at risk for T2D include individuals 45 years of age and older; individuals with insulin-resistance or impaired glucose tolerance; younger individuals who are obese (>120% desirable body weight or a body mass index $\geq 27$): individuals who have a first-degree relative with diabetes; individuals who are members of a high-risk ethnic population (African American, Hispanic American, Native American, Asian American); women who have delivered a baby weighing more than 9 lbs; individuals who have previously had gestational diabetes mellitus (GDM); individuals who are hypertensive (blood pressure $\geq 140/90$ mm Hg); individuals who have atherogenic dyslipidemia (high-density lipoprotein [HDL] cholesterol levels $\leq 35$ mg/dl or triglyceride levels $\geq 250$ mg/dl); or individuals who have had impaired glucose tolerance (IGT) or impaired fasting glucose (IFG) on previous testing.

EXAMPLES

The invention is further described in the following examples, which do not limit the scope of the invention described in the claims.

Example 1

Haplotype-Tagging Polymorphisms at the Adiponectin Receptor 1 (ADIPOR1) Locus are Associated with Lower Gene Expression and Increased Cardiovascular Risk in Type 2 Diabetes A polymorphism at the ADIPOR1 locus (rs7539542) has recently been associated (Wang et al., Diabetes, 53(8):2132-6 (2004)) with an alteration in ADIPOR1 mRNA levels. The aim of this study was to comprehensively evaluate the role of ADIPOR1 polymorphisms as determinants of CAD risk in type 2 diabetes.

Methods

Study subjects. The study population included two populations of Caucasian subjects with type 2 diabetes, one from Boston, Mass. (n=411) and the other from San Giovanni Rotondo, Italy (n=533). Each population included a group of cases with angiographically defined CAD (defined as subjects who had a stenosis greater than 50% in at least one major coronary artery or their main branches; n=207 and n=219 in Boston and Italy, respectively) and a group of controls with negative CAD history and stress test.

In Boston, the CAD-positive cases—defined as subjects who had a stenosis greater than 50% in at least one major coronary artery or their main branches—were recruited among type 2 diabetic patients who underwent cardiac catheterization. Controls were diabetic patients aged 55 years or more, who had diabetes for five years or more but had a negative cardiovascular history and a normal exercise treadmill test (ETT).

The Italian population also consisted of type 2 diabetic patients. Cases were patients who had angiographic evidence of stenosis greater than 50% in at least one major coronary artery or their main branches, or who had acute myocardial infarction. Controls included diabetic patients without symptoms and with normal resting ECG and ETT or with coronary stenosis (at angiography) ≦50%. Clinical features of cases and controls from the two studies are shown in Table 1.

TABLE 1

Clinical characteristics of CAD cases and controls with type 2 diabetes from Boston and from Italy.

| | Boston | | Italy | |
|---|---|---|---|---|
| | CAD − | CAD + | CAD − | CAD + |
| N | 204 | 207 | 314 | 219 |
| Males (%) | 57.3 | 65.7 | 41.9 | 67.0 |
| Age (yrs) | 65 ± 7 | 65 ± 7 | 60 ± 8 | 65 ± 8 |
| Age at Diabetes Dx (yrs) | 52 ± 8 | 53 ± 10 | 49 ± 11 | 50 ± 11 |
| Diabetes Duration (yrs) | 13 ± 6 | 12 ± 8 | 11 ± 8 | 15 ± 9 |
| % IBW (%) | 145 ± 27 | 144 ± 30 | 145 ± 27 | 135 ± 24 |
| HbA1c (%) | 7.2 ± 1.2 | 7.3 ± 1.3 | 8.5 ± 1.9 | 8.7 ± 1.9 |
| Treatment | | | | |
| Diet Only (%) | 7.1 | 10.1 | 9.9 | 6.8 |
| Oral Agents (%) | 54.0 | 46.9 | 52.0 | 34.8 |
| Insulin (%) | 38.9 | 43.0 | 38.1 | 57.2 |
| Hypertension (%) | 76.5 | 81.4 | 75.6 | 77.0 |
| Ever Smoked (%) | 70.6 | | 28.2 | 40.3 |

Data are % or means ± SD; % IBW = % Ideal Body Weight

The European diversity panel of the Joslin Genetics Core, consisting of healthy subjects from Italy (n=192), Poland (n=180), and the UK (n=192), was also typed to evaluate population stratification as a plausible explanation of association findings.

SNP genotyping. SNPs for the linkage disequilibrium study were typed in the Caucasian HapMap panel by means of PCR followed by single base extension/fluorescence polarization (AycloPrime-FP SNP Detection System) using a Wallac VICTOR² Multilabel Plate Reader (Perkin-Elmer, Boston, Mass.). Haplotype-tagging polymorphisms were also typed in the study groups by single base extension/fluorescence polarization, with the exception of rs7539542, which was typed by means of a TaqMan assay (Applied Biosystems, Foster City, Calif.) implemented on an ABI PRISM 7700 HT Sequence Detection System. Genotyping quality was tested by including six blinded duplicate samples in each 96-well assay. The average agreement rate of duplicate samples was >99%. Sequences of the primers and probes used for typing are available from the authors.

Data analysis. Genotype distributions were tested at each polymorphic locus for departure from Hardy-Weinberg equilibrium. Pairwise linkage disequilibrium coefficients (D' and $r^2$) were estimated and plotted using the Haploview software package (Barret et al., Bioinformatics 21:263-265, 2005). Linkage disequilibrium blocks were determined according to the confidence interval method using the Gabriel criteria (Gabriel et al., Science 296:2225-2229, 2002). Haplotype frequency and haplotype-tagging SNPs were determined by means of the algorithms implemented in the Haploview software (24), using 0.05 as the frequency threshold to define common haplotypes.

Allele frequencies were compared between cases and controls within each population by chi-square tests and in the two populations combined by the Mantel-Haenszel statistics. P values were adjusted for multiple comparisons by the Bonferroni correction, considering conservatively that six independent comparisons, corresponding to the six haplotype-tagging SNPs, were made. False discovery rates (FDRs) were calculated from the equation p*k/i, where p is the p value, k is the number of comparisons, and i is the p value ranking. The significance of between-population differences in the association with CAD was determined by means of the Breslow-Day test. For each SNP, the odds ratios of CAD for heterozygotes and minor allele homozygotes as compared to major allele homozygotes were estimated by logistic regression analysis using two different models: one including only the genotypes as predictors, the other also including known cardiovascular risk factors (age, gender, % IBW, smoking status, hypertension status, and HbA1c) as covariates. In the analysis of the two populations combined, an indicator variable for the study population (Boston vs. Italy) was added to both models. Between-population differences in the CAD risk associated with each genotype were tested for significance by adding an interaction term (genotype*population) to the logistic regression models.

Maximum likelihood estimates of haplotype frequencies in cases and controls were derived using the EM algorithm as implemented in the function haplo.em of the Haplo Stats suite (27). The association between CAD and common (≧0.05) ADIPOR1 haplotypes was analyzed using the score statistics proposed by Schaid et al. and implemented in the function HAPLO. SCORE of the Haplo Stats software (27). This method allows adjustment for covariates (in this case, age, gender, % ideal body weight [IBW], smoking status, hypertension status, HbA1c, study population) and provides a global test of association as well as haplotype-specific tests. After testing for association with haplotypes, a combination of haplotypes (i.e., a diplotype) was assigned to each individual on the basis of the posterior probabilities of the different phases. The risk of CAD associated with each diplotype relative to CCG/CCG reference homozygotes at SNPs rs7539542, rs10920531, and rs4950894, respectively, was then estimated by logistic regression analysis as described above for individual SNPs. Forty-three subjects (4.6% of the total) were excluded from this analysis because none of the possible phases had a posterior probability greater than 0.70.

Results

The ADIPOR1 gene is located on chromosome 1q32 and includes eight exons encompassing 17.5 kb. To select markers that would capture comprehensively the variability at this locus, the Caucasian ('CEU') HapMap panel was typed for 15 common SNPs (MAF≧5%) covering the entire gene plus 5 Kb on each side (a list of the SNPs and their positions is provided in the On-Line Data Supplement). Data were then integrated with those of 13 other SNPs typed by the HapMap initiative (HapMap Public Release #19) (Altshuler et al., Nature 437:1299-1320, 2005). Linkage disequilibrium analysis of the resulting set of 28 SNPs (1 Kb average spacing, listed in Table 2) revealed two LD blocks as defined according to the confidence interval criteria proposed by Gabriel et al. (Science 296:2225-2229, 2002).

TABLE 2

Characteristics of the polymorphisms that were used to determine the LD structure of the ADIPOR1 locus

| RefSNP/Celera ID | Position† | Variation | Frequency‡ | Location |
|---|---|---|---|---|
| rs2232852§ | −11800 | G > T | 0.337 | 5' flanking |
| rs2232853 | −11760 | C > T | 0.330 | 5' flanking |
| rs2232854 | −11641 | C > T | 0.330 | 5' flanking |
| rs10920535 | −9494 | A > G | 0.330 | 5' flanking |
| rs6666089 | −8505 | C > T | 0.344 | 5' flanking |
| rs7529354 | −7303 | G > A | 0.143 | 5' flanking |
| rs7514221§ | −6315 | A > G | 0.457 | Intron1 |
| rs10920533§ | −5620 | G > A | 0.326 | Intron1 |
| rs1539355 | −3882 | T > C | 0.340 | Intron1 |
| rs10800886§ | −2193 | C > T | 0.263 | Intron1 |
| rs10494839§ | −1896 | G > A | 0.340 | Intron1 |
| rs12733285 | −1742 | G > A | 0.309 | Intron1 |
| rs2275738 | −106 | G > A | 0.457 | Intron1 |
| rs2275737§ | −102 | G > T | 0.457 | Intron 1 |
| rs16850799§ | 348 | G > A | 0.202 | Intron 2 |
| hCV437592 | 3002 | C > T | 0.202 | Intron 3 |
| rs12045862§ | 3393 | C > T | 0.202 | Intron 3 |
| rs1342386 | 5646 | A > G | 0.468 | Intron 4 |
| rs1342387 | 5843 | G > A | 0.468 | Intron 4 |
| hCV37351 | 7479 | C > T | 0.191 | Intron 6 |
| rs7539542 | 10225 | C > G | 0.277 | Exon 8 -3'UTR |
| rs10920531 | 11363 | C > A | 0.319 | 3' flanking |
| rs4336908§ | 11663 | G > A | 0.174 | 3' flanking |
| rs6688148 | 13555 | C > A | 0.298 | 3' flanking |
| rs2185781§ | 13693 | G > A | 0.181 | 3' flanking |
| rs1578679§ | 14949 | A > G | 0.322 | 3' flanking |

TABLE 2-continued

Characteristics of the polymorphisms that were used to determine the LD structure of the ADIPOR1 locus

| RefSNP/Celera ID | Position† | Variation | Frequency‡ | Location |
|---|---|---|---|---|
| rs4950894§ | 15671 | A > G | 0.383 | 3' flanking |
| rs6683480§ | 16402 | A > G | 0.276 | 3' flanking |

†Relative to the translation start site on the July 2004 Human Genome assembly (hg17).
‡Frequency of the allele indicated on the right in the 'Variation' column.
§ Genotype data from the HapMap database.
¶This SNP is also known as rs1139646.

Figure 1B:
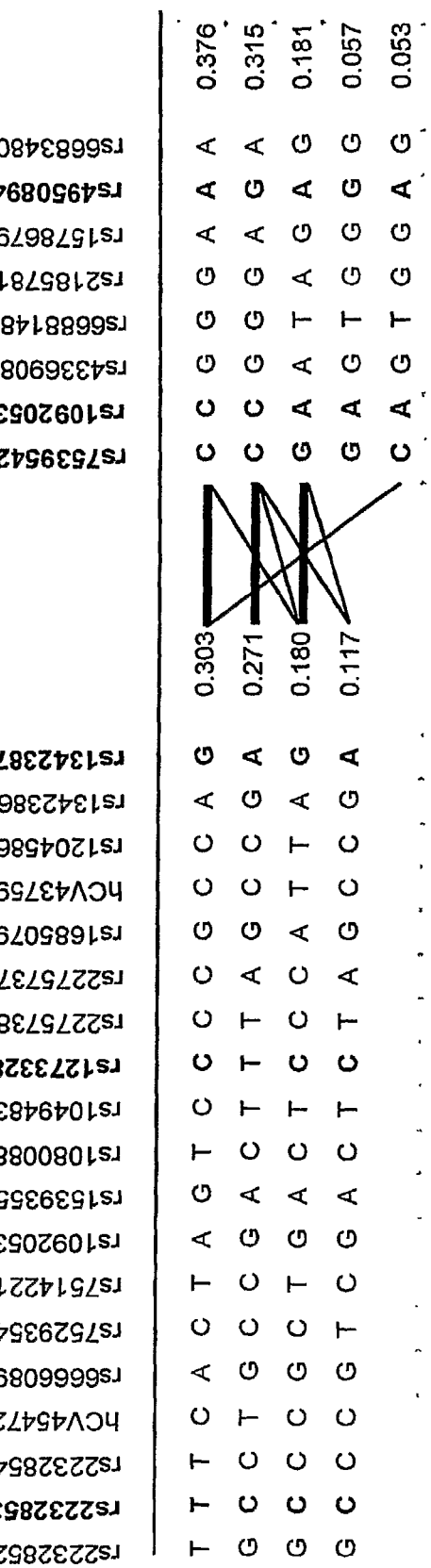
FIG. 1B is a table of haplotypes with a frequency ≧5% in the two linkage disequilibrium blocks. Haplotype frequency and haplotype-tagging SNPs (in bold) were determined by means of the algorithms implemented in the Haploview software (Barret et al, Bioinformatics. 21:263-265, 2005).

One block extends from the 5' flanking region (−11800 bp from the translation start site) to intron 4 (+5843), and the other is at the 3' end of the gene (FIG. 1A). One SNP—hCV37351—is between the two blocks and exhibits significant LD with both (FIG. 1A). Based on this LD structure, six polyinorphisms were selected for association studies, three tagging the first block (rs2232853, rs12733285, and rs1342387) and three tagging the second (rs7539542, rs10920531, and rs4950894) (FIG. 1B).

The association between these six SNPs and coronary artery disease (CAD) was evaluated in two populations of Caucasian individuals with type 2 diabetes, one from Boston and the other from Italy. The two populations were similar with respect to age at examination, age at diagnosis and treatment of diabetes, and body weight (Table 1). Subjects from Boston had on average better glycemic control and a higher prevalence of former or current smokers than those from Italy (Table 1). In both populations, the prevalence of smoking was markedly higher in cases than controls, consistent with the known, powerful effect of this factor on cardiovascular risk. The two populations combined provided more than 80% power ($\alpha$=0.05) to detect genetic effects with allelic odds ratios ranging from 1.3 for rs1342387 to 1.4 for less frequent SNPs such as rs2232853 or rs7539542.

Genotype distributions were in Hardy-Weinberg equilibrium at all six loci. The three SNPs tagging the 5' block had similar allele frequencies in cases and controls in both populations (Table 3). By contrast, the three tags of the 3' LD block (rs7539542, rs10920531, and rs4950894) were all significantly associated with CAD in the Boston population, with nominal p values ranging from 0.001 to 0.01 (Table 3). In the Italian cases and controls, the smaller differences in allele frequencies for these three polymorphisms were not statistically significant (Table 3), but neither were they significantly different from the allele frequency differences in the Boston population (p=0.19, p=0.14, and p=0.21, respectively, for the difference in association in the two study populations [Breslow-Day test]).

TABLE 3

Minor allele frequencies of the six ADIPOR1 ht-SNPs in the study groups.

| | | Boston | | | Italy | | | Boston + Italy§ | | |
|---|---|---|---|---|---|---|---|---|---|---|
| SNP | Minor Allele | CAD− (n = 408) | CAD+ (n = 414) | p† | CAD− (n = 628) | CAD+ (n = 438) | p† | CAD− (n = 1036) | CAD+ (n = 852) | P†‡ |
| rs2232853 | T | 0.270 | 0.275 | 0.88 | 0.299 | 0.294 | 0.87 | 0.287 | 0.285 | 0.99 |
| rs12733285 | T | 0.356 | 0.355 | 0.99 | 0.415 | 0.401 | 0.64 | 0.393 | 0.379 | 0.67 |
| rs1342387 | A | 0.500 | 0.470 | 0.39 | 0.505 | 0.488 | 0.60 | 0.504 | 0.479 | 0.31 |
| rs7539542 | G | 0.280 | 0.367 | 0.009 | 0.296 | 0.325 | 0.32 | 0.290 | 0.345 | 0.004 |
| rs10920531 | A | 0.330 | 0.444 | 0.001 | 0.373 | 0.420 | 0.12 | 0.356 | 0.431 | 0.0009 |
| rs4950894 | G | 0.376 | 0.283 | 0.006 | 0.347 | 0.310 | 0.22 | 0.358 | 0.297 | 0.006 | n = number of chromosomes.
§At each polymorphic locus, the association with CAD was not significantly different in the two populations.
†1 d.f.
‡Mantel-Haenszel statistics.

When the two populations were pooled and analyzed together using the Mantel-Haenszel statistics, all three loci were significantly associated with CAD, with nominal p values of 0.004 for rs7539542, 0.0009 for rs10920531, and 0.006 for rs4950894 and Bonferroni-adjusted p values of 0.024, 0.005, and 0.036, respectively. The corresponding False Discovery Rates (FDR) were 0.011, 0.005, and 0.012, respectively. For both rs7539542 and rs10920531, the allelic association was mostly due to an excess of minor allele homozygotes among cases. For rs10929531, this effect was significant in both populations (adjusted OR=3.8, 95% CI 1.9-7.6 and 1.8, 95% CI 1.05-3.2 in Boston and Italy, respectively). The ORs were not significantly different between the two populations and when the two studies were combined, minor allele homozygotes were estimated to have a more than two-fold increase in the odds of CAD as compared to major allele homozygotes (Table 4). A weak, non-significant effect was noted for heterozygotes, with common OR estimates of 1.2-1.3 (Table 4). In the case of rs4950894, both heterozygotes and minor allele homozygotes were significantly associated with protection from CAD, with adjusted ORs of 0.72 and 0.57, respectively (Table 4).

To assess whether population stratification might be responsible for the stronger association with CAD in Boston, the frequencies of the risk alleles were determined in a sample of healthy individuals from three European ethnic groups (Italian, n=192, Polish, n=180, and British, n=192), reasoning that stratification was an unlikely explanation of the findings described herein if allele frequencies varied little among European populations. As shown in Table 5, the allele frequencies of all three SNPs displaying association with CAD were not significantly different among European populations. At rs10920531 (the SNP showing the strongest association with CAD), the difference in allele frequencies between Boston cases and controls was significantly bigger than the largest difference in allele frequencies between European populations (0.114 vs. 0.038, p<0.05). Furthermore, the frequency of the risk allele in Boston CAD cases was significantly higher than the highest allele frequency observed in the European populations (0.444 vs. 0.362, p<0.025).

TABLE 4

Odds ratios (OR) for the association between coronary artery disease (CAD) and SNPs in the 3' ADIPOR1 block.

| Polymorphism | Boston | | Italy | | Boston + Italy§ | |
|---|---|---|---|---|---|---|
| | Unadjusted OR | Adjusted OR† | Unadjusted OR | Adjusted OR† | Unadjusted OR‡ | Adjusted OR†‡ |
| rs7539542 | | | | | | |
| C/G | 1.17 (0.8-1.8) | 1.27 (0.8-2.0) | 1.10 (0.8-1.6) | 1.21 (0.8-1.9) | 1.13 (0.9-1.5) | 1.16 (0.9-1.55) |
| G/G | 3.12 (1.5-6.6) | 4.28 (1.9-9.6) | 1.39 (0.75-2.6) | 1.48 (0.75-2.9) | 1.95 (1.2-3.1) | 2.26 (1.4-3.7) |
| rs10920531 | | | | | | |
| C/A | 1.40 (0.9-2.2) | 1.53 (0.95-2.4) | 1.13 (0.8, 1.7) | 1.17 (0.8, 1.8) | 1.2 (0.9-1.7) | 1.25 (0.9-1.7) |
| A/A | 2.89 (1.5-5.5) | 3.81 (1.9-7.6) | 1.52 (0.9, 2.5) | 1.82 (1.05-3.2) | 1.96 (1.3-2.9) | 2.26 (1.5-3.4) |
| rs4950894 | | | | | | |
| A/G | 0.61 (0.40-0.93) | 0.53 (0.34-0.83) | 0.85 (0.58, 1.24) | 0.86 (0.56, 1.31) | 0.74 (0.56-0.97) | 0.72 (0.53-0.97) |
| G/G | 0.44 (0.22-0.89) | 0.37 (0.17-0.78) | 0.74 (0.42, 1.31) | 0.83 (0.44-1.56) | 0.60 (0.39-0.94) | 0.57 (0.36-0.92) |

Odds ratios were computed using major allele homozygotes as the reference group. Values in parentheses are 95% confidence intervals.
§None of the odds ratios were significantly different between the two study populations.
†Adjusted for age, gender, % IBW, smoking status, hypertension status, and HbA1c.
‡Adjusted for study population (Boston vs. Italy)

TABLE 5

Risk allele frequencies in the Boston study and three European populations.

| | Boston | | European Populations | | | | |
|---|---|---|---|---|---|---|---|
| | CAD− (n = 408) | CAD+ (n = 414) | Italy (n = 384) | Poland (N = 360) | UK (n = 384) | D1 | D2 |
| rs7539542 | 0.280 | 0.367 | 0.284 | 0.322 | 0.320 | 0.049 | 0.045 |
| rs10920531 | 0.330 | 0.444 | 0.362 | 0.346 | 0.362 | 0.098* | 0.082** |
| rs4950894 | 0.624 | 0.717 | 0.604 | 0.621 | 0.664 | 0.033 | 0.053 |

D1 = Difference between the case-control difference in risk allele frequencies and the greatest difference in risk allele frequencies between European populations.
D2 = Difference between risk allelic frequency in cases and the highest allele frequency in the European populations.
*p < 0.05;
**p < 0.025

Thus, population stratification was an unlikely explanation of the findings described herein. Differences in clinical characteristics such as age, gender, HbA1c, or smoking history are unlikely to be responsible for the different strength of the association in the two populations, as no significant interaction between these variables and SNPs was found (see Table 6).

TABLE 6

Allelic OR of CAD for rs10920531 in the two populations stratified by sex, age, HbA1c levels, and smoking history.

|  |  | Boston | | Italy | |
|---|---|---|---|---|---|
|  |  | OR | 95% CI | OR | 95% CI |
| Sex | M | 1.47 | 1.0-2.1 | 1.25 | 0.9-1.75 |
|  | F | 1.89 | 1.2-3.0 | 1.07 | 0.7-1.6 |
| Age | ≦65 | 1.49 | 1.0-2.2 | 1.50 | 1.1-2.1 |
|  | >65 | 1.85 | 1.2-2.8 | 1.00 | 0.6-1.5 |
| HbA1c | ≦7 | 1.74 | 1.1-2.6 | 1.10 | 0.6-1.8 |
|  | >7 | 1.63 | 1.1-2.5 | 1.24 | 0.9-1.7 |
| Smoking | No | 1.62 | 1.0-2.6 | 1.16 | 0.8-1.6 |
|  | Yes | 1.96 | 1.3-3.0 | 1.39 | 0.9-2.1 |

Figures 2A, 2B:
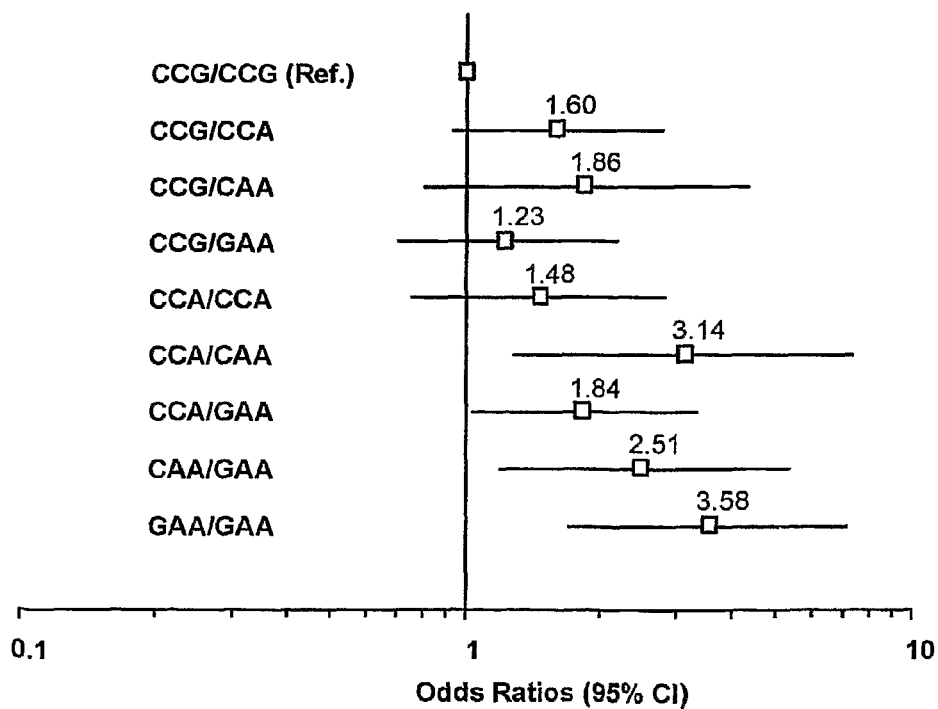
FIG. 2A is a table of haplotype frequencies in CAD-positive cases and CAD-negative controls. Positive and negative scores denote an association with increased and decreased risk of CAD, respectively. Haplotype specific p-values are reported along with the global p-value.
FIG. 2B is a graph illustrating Odds Ratios of CAD associated with different haplotype combinations (diplotypes). Odds ratios are indicated by the squares, 95% confidence interval by the lines.

Consistent with the individual SNP analyses, a significant association with CAD was observed for the haplotypes in the 3' block, but not for those in the 5' block. FIG. 2A shows the maximum likelihood estimates of the 3' block haplotypes in the combined cases and controls along with their score statistics for association with CAD as computed by the HAPLO.SCORE program (27). Haplotype distributions were significantly different in cases and controls (global empirical p=0.0002). Haplotype 'CCG', which exactly corresponds to the minor allele of rs4950894; the minor allele of rs4950894 is only observed in conjunction with a C at the other two SNPs, was associated with protection from CAD (haplotype-specific empirical p=0.00035), whereas haplotype GAA, exactly corresponding to the minor allele of rs7539542, was associated with predisposition (p=0.021). A predisposing effect was also observed for haplotype 'CAA', although the p-value did not reach significance (p=0.11) due to the low frequency of this haplotype. When diplotypes were assigned to each subject, haplotypes 'GAA' and 'CAA' were significantly associated with an increase risk of CAD when they occurred as homozygotes, in combination with each other, or in combination with the neutral haplotype 'CCA' (FIG. 2B). The ORs of CAD for these genotypes as compared to 'CCG/CCG' homozygotes ranged from 1.8 to 3.6. The ORs were lower and did not differ significantly from 1.0 when haplotypes 'GAA' and 'CAA' occurred as heterozygotes with the protective haplotype 'CCG' (FIG. 2B).

Example 2

Levels of ADIPOR1 mRNA in Peripheral Blood Mononuclear Cells

Resequencing of all exons in 32 CAD-positive cases did not identify any missense polymorphism in linkage disequilibrium with rs7539542, rs10920531, or rs4950894. Thus, the association with CAD may be mediated by an effect of the polymorphisms on gene expression.

Methods

To investigate this possibility, levels of ADIPOR1 mRNA were measured by quantitative, real time PCR in peripheral blood mononuclear cells (PBMC) from 60 non-diabetic employees of the Joslin Diabetes Center (mean age=33±11 years, BMI=25.9±3.8 Kg/m$^2$) and in adipose tissue biopsies from 28 obese subjects who underwent liposuction or gastric bypass surgery at Washington University (mean age=44±10 year, BMI=45.2±12 Kg/m$^2$). PBMC were isolated from peripheral blood by density gradient (Vacutainer CPT, Beckton-Dickinson Franklin Lakes, N.J.); subcutaneous abdominal adipose tissue was obtained by percutaneous needle aspiration. RNA was extracted using the RNeasy Kit (Qiagen, Valencia, Calif.). ADIPOR1 mRNA levels relative to GAPDH mRNA levels were determined by quantitative RT-PCR using pre-developed TaqMan Gene Expression Assays from Applied Biosystems (Foster City, Calif.) according to the manufacturer's instructions in an ABI PRISM 7700 HT Sequence Detection System. ADIPOR1/GAPDH mRNA ratios were obtained from the equation $2^{-\Delta CT}$, where $\Delta CT$ is the difference in threshold cycles between ADIPOR1 and GAPDH. At each polymorphic locus, the significance of mRNA level differences between genotypes was estimated by ANCOVA using log-transformed values to account for the skewed distribution of the ADIPOR1/GAPDH ratios and age and gender as covariates.

Results

Figure 3A:
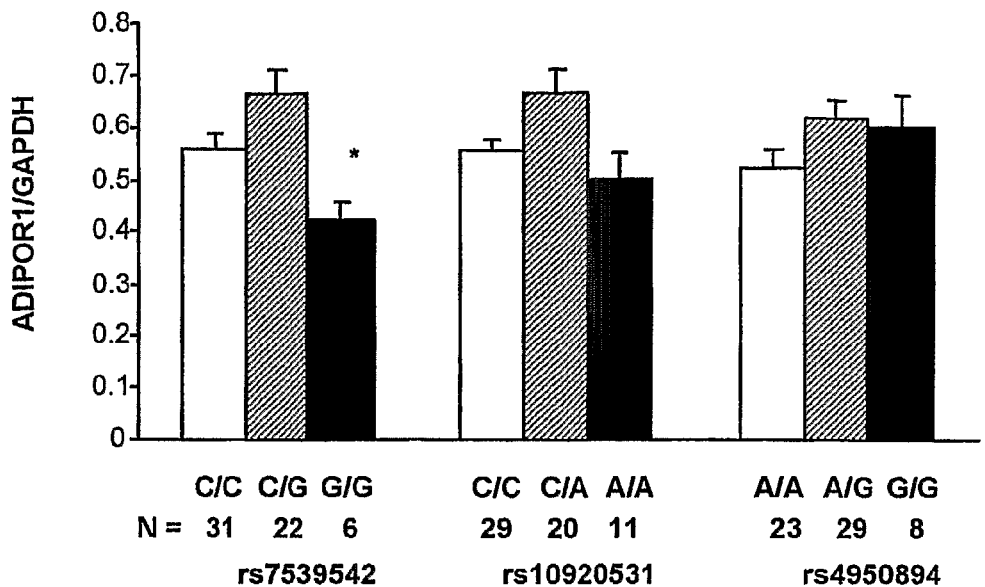
FIG. 3A is a bar graph showing ADIPOR1/GAPDH ratios in peripheral blood mononuclear cells (PBMC). Results are means±SE. *p=0.001 for GIG vs. C/G and p=0.014 for GIG vs. C/C.
Figure 3B:
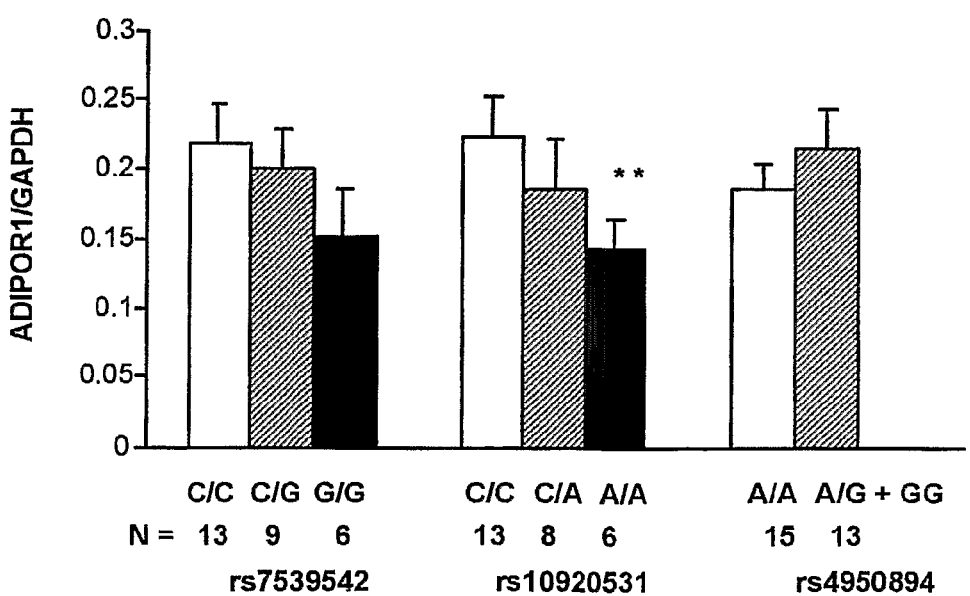
FIG. 3B is a bar graph showing ADIPOR1/GAPDH ratios in adipose tissue biopsies. Results are means±SE. The number of individuals in each genotype group is indicated below each bar. There was only one subject in the adipose biopsy group who was G/G homozygous at rs4950894; this subject was considered together with A/G heterozygotes. **p=0.013 for A/A vs. C/C.

Both in mononuclear cells and adipose tissue, some of the genotypes associated with increase predisposition to CAD (i.e. minor allele homozygotes for rs7539542 or rs10920531, major allele homozygotes for rs4950894) had lower levels of ADIPOR1 mRNA (FIG. 3). In mononuclear cells, this pattern was significant for SNP rs7539542, where G/G homozygotes had 30-40% lower ADIPOR1 mRNA levels than heterozygotes or C/C homozygotes (p=0.001 and p=0.014, respectively) (FIG. 3A). When the three SNPs were considered together as haplotypes, the CAD-predisposing 'GAA/GAA' genotype (for rs7539542-rs10920531-rs4950894) was associated with significantly lower ADIPOR1 mRNA levels than the CAD-protecting 'CCG/CCG' genotype (0.42 vs. 0.61, p=0.007). In the adipose tissue biopsies, the difference in ADIPOR1 mRNA levels among genotypes was significant for SNP rs10920531, where minor allele homozygotes had 35% lower expression than major allele homozygous (p=0.013), with heterozygotes having intermediate values (FIG. 3B).

Example 3

Effect of SNP rs7539542 on ADIPOR1 mRNA Stability

Of the three tagging SNPs, rs7539542 was especially attractive as a possible functional variant because of its location in the 3' UTR, a region that in many genes plays a pivotal role in the control of gene expression by binding proteins that regulate mRNA processing, translation or degradation (Conne et al., Nat Med 6:637-641, 2000, Day and Tuite, J Endocrinol 157:361-371, 1998).

Methods

HEK293 cells were transfected with allelic forms of ADIPOR1 cDNA, and mRNA levels were measured at different time points after stopping transcription with actinomycin D. AdipoR1 cDNA expression constructs carrying the two alleles of rs7539542 (pCMV-SPORT6-AdipoR1/G and pCMV-SPORT6-AdipoR1/C, respectively) were prepared by site-directed mutagenesis (QuickChange II XL Kit, Stratagene, La Jolla, Calif.) starting from ADIPOR1 IMAGE clone #3878067 (GeneBank # BC010743) (ATCC, Manassas, Va.). HEK293 cells were cultured in 175-cm$^2$ culture flasks with DMEM/F12 containing 10% (vol/vol) FCS, 2 mM glutamine at 37° C. in a humidified atmosphere of 5% $CO_2$. Cells were plated in six well plates, grown in complete medium for 48 h, and transfected with either pCMV-SPORT6 AdipoR1/C or pCMV-SPORT6 AdipoR1/G using FuGENE 6 Transfection Reagent (Roche Diagnostic, Italia) according to manufacturer's instructions. Eighteen hours after transfection, Actinomycin D (5 mg/ml) was added and total RNA extracted at different time points using the RNAEasy Quick kit (Qiagen, Italia). ADIPOR1 mRNA levels relative to GAPDHmRNA levels were determined by quantitative RT-PCR using a pre-developed TaqMan Gene Expression Assay from Applied Biosystems (Applied Biosystems, Italia) according to the manufacturer's instructions in an ABI PRISM 7700 HT Sequence Detection System.

Results

Figure 4:
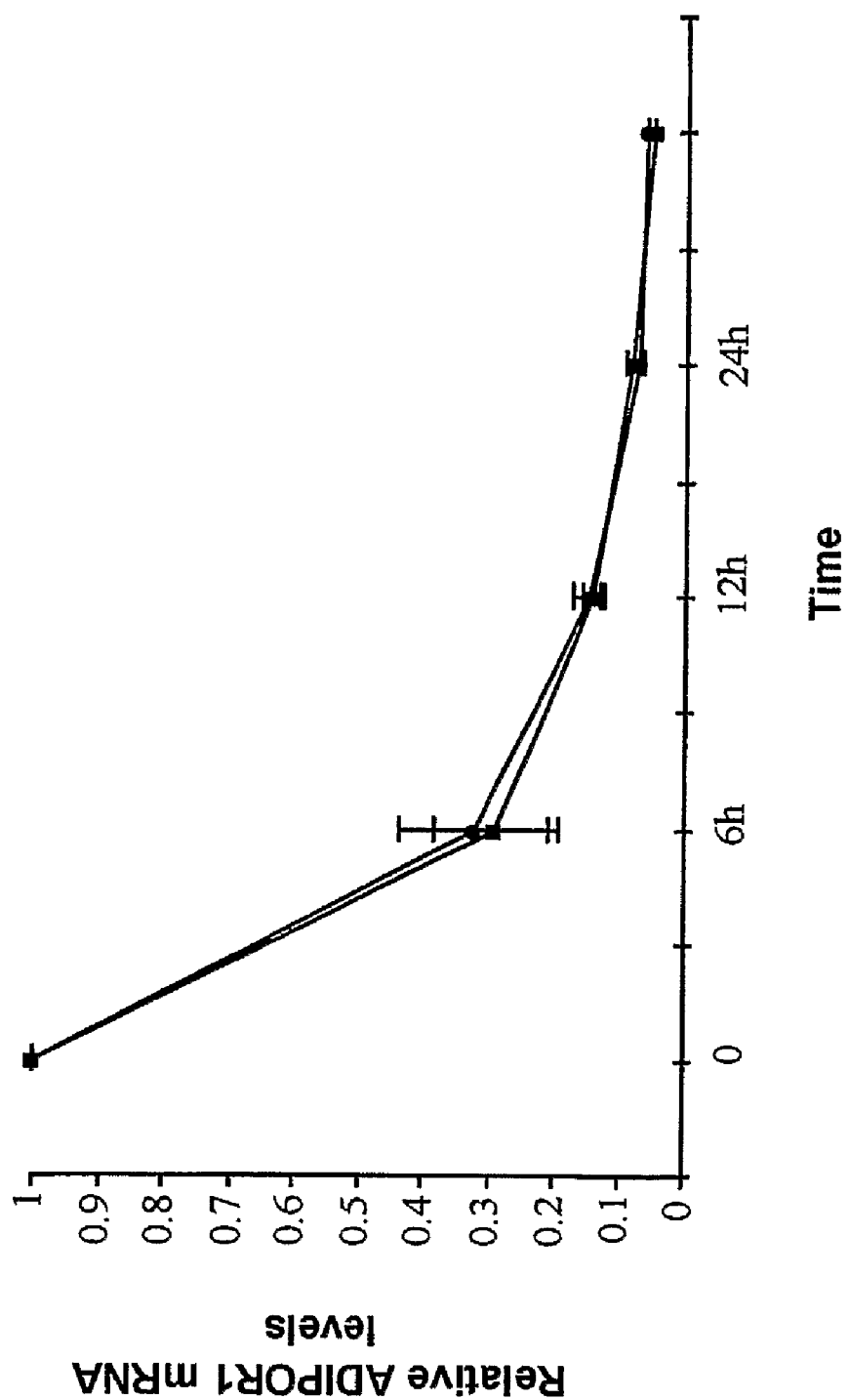
FIG. 4 is a graph illustrating the effect of rs7539542 on ADIPOR1 mRNA stability. HEK293 cells were transfected with either pCMV-SPORT6 AdipoR1/C (circles) or pCMV-SPORT6 AdipoR1/G (squares) and treated with Actinomycin-D. AdipoR1 mRNA levels were measured by RT-PCR at different time points, normalized to the expression of GAPDH, and expressed as proportions of the levels at time 0. Data are means±SD of three independent experiments.

As shown in FIG. 4, the rates of mRNA decay were virtually identical for the two alleles, indicating that rs7539542 does not affect mRNA stability, at least in this cell type. While these findings should be interpreted with caution because of the tissue-specific nature of the regulation of mRNA stability, it is likely that the functional variants are placed elsewhere, for instance in as yet unknown 3' flanking regulatory elements.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of evaluating a subject for risk of developing cardiovascular disease, the method comprising:
   providing a sample comprising genomic DNA from the subject;
   detecting the presence, in one or both copies of an adiponectin receptor 1 (ADIPOR1) gene of the subject, an "A" allele at polymorphism rs10920531; and
   determining that the subject has an increased risk of developing cardiovascular disease based on the presence of an "A" allele at polymorphism rs10920531.

2. The method of claim 1, further comprising detecting the presence, in one or both copies of the ADIPOR1 gene of the subject, one or more of:
   a polymorphism at rs4950894; and
   a polymorphism at rs7539542.

3. The method of claim 2, comprising detecting the presence, in one or both copies of the ADIPOR1 gene of the subject, one or more of:
   a "G" allele at polymorphism rs7539542; or
   an "A" allele at polymorphism rs4950894,
   determining that the subject has an increased risk for developing cardiovascular disease based on the presence of one or more of a "G" allele at polymorphism rs7539542 or an "A" allele at polymorphism rs4950894.

4. The method of claim 1, wherein the detecting step comprises using an oligonucleotide complementary to a polynucleotide spanning the nucleotide at rs10920531.

5. The method of claim 1, wherein the subject has a family history of cardiovascular disease.

6. The method of claim 1, wherein the cardiovascular disease is coronary artery disease (CAD).

7. The method of claim 1, wherein the cardiovascular disease is atherosclerosis, ischemic heart disease, atherosclerosis, angina, or myocardial infarction.

8. The method of claim 1, wherein the subject has a family history of type 2 diabetes or has been diagnosed with type 2 diabetes.

9. The method of claim 1, wherein the detecting step comprises using a probe or primer that hybridizes under high stringency conditions to a nucleic acid sequence spanning the nucleotide.

10. The method of claim 2, wherein the detecting step comprises using an allele-specific oligonucleotide selected from the group consisting of:
    an oligonucleotide complementary to a polynucleotide spanning the nucleotide at rs7539542; and
    an oligonucleotide complementary to a polynucleotide spanning the nucleotide at rs4950894.

11. The method of claim 2, wherein the detecting step comprises using a probe or primer that hybridizes under high stringency conditions to a nucleic acid sequence spanning the one or more nucleotides.

* * * * *